US010807995B2

(12) United States Patent
Aquila et al.

(10) Patent No.: US 10,807,995 B2
(45) Date of Patent: Oct. 20, 2020

(54) THIENOTHIOPHENE COMPOUNDS FOR LONG-ACTING INJECTABLE COMPOSITIONS AND RELATED METHODS

(71) Applicant: Alkermes Pharma Ireland Limited, Dublin (IE)

(72) Inventors: Brian M. Aquila, Marlborough, MA (US); Hoan Huynh, Waltham, MA (US); Lewis D. Pennington, Arlington, MA (US); Ingo Mugge, Waltham, MA (US); Baudouin Gerard, Arlington, MA (US); Markus Haeberlein, Wellesley, MA (US); Roman A. Valiulin, Cambridge, MA (US); Julius F. Remenar, Framingham, MA (US); Demetri T. Moustakas, Belmont, MA (US); Thomas Andrew Wynn, Lexington, MA (US); Todd Bosanac, New Milford, CT (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

(21) Appl. No.: 16/508,697

(22) Filed: Jul. 11, 2019

(65) Prior Publication Data
US 2020/0017529 A1 Jan. 16, 2020

Related U.S. Application Data

(60) Provisional application No. 62/697,899, filed on Jul. 13, 2018, provisional application No. 62/699,290, filed on Jul. 17, 2018.

(51) Int. Cl.
C07D 519/00 (2006.01)
A61K 9/00 (2006.01)
(52) U.S. Cl.
CPC .......... *C07D 519/00* (2013.01); *A61K 9/0019* (2013.01)
(58) Field of Classification Search
CPC ................................ C07D 519/00; A61K 9/00
USPC .......................................................... 546/43
See application file for complete search history.

(56) References Cited

U.S. PATENT DOCUMENTS

| | | | |
|---|---|---|---|
| 3,828,050 A | 8/1974 | Buckett et al. | |
| 4,356,024 A | 10/1982 | Dickore' et al. | |
| 4,668,685 A | 5/1987 | Shami | |
| 4,673,679 A | 6/1987 | Aungst et al. | |
| 6,150,524 A | 11/2000 | Hartmann et al. | |
| 6,225,321 B1 | 5/2001 | Hu et al. | |
| 6,376,548 B1 | 4/2002 | Mulvihill et al. | |
| 6,440,987 B1 | 8/2002 | Nagase et al. | |
| 6,716,452 B1 | 4/2004 | Piccariello et al. | |
| 7,230,005 B2 | 6/2007 | Shafer et al. | |
| 7,538,118 B2 | 5/2009 | Schütz et al. | |
| 7,655,671 B2 | 2/2010 | Schmidharnmer et al. | |
| 7,759,358 B2 | 7/2010 | Crooks et al. | |
| 8,258,298 B2 | 9/2012 | Dlubala et al. | |
| 8,455,509 B2 | 6/2013 | Dlubala | |
| 8,461,171 B2 | 6/2013 | Holaday et al. | |
| 8,653,271 B2 | 2/2014 | Stinchcomb et al. | |
| 8,916,170 B2 | 12/2014 | Palma et al. | |
| 8,962,647 B1 | 2/2015 | Guo et al. | |
| 9,006,262 B2 | 4/2015 | Suzuki et al. | |
| 9,040,032 B2 | 5/2015 | Jenkins et al. | |
| 9,309,256 B2 | 4/2016 | Singh | |
| 9,321,780 B2 | 4/2016 | Singh | |
| 9,480,665 B2 | 11/2016 | Singh | |
| 9,549,924 B2 | 1/2017 | Singh | |
| 2003/0022876 A1 | 1/2003 | Ashton et al. | |
| 2003/0105120 A1 | 6/2003 | Hu et al. | |
| 2004/0254182 A1 | 12/2004 | Mulvihill et al. | |
| 2009/0017102 A1 | 1/2009 | Stinchcomb et al. | |
| 2009/0137618 A1 | 5/2009 | Jenkins | |
| 2010/0068786 A1 | 3/2010 | Chmielewski et al. | |
| 2011/0245287 A1 | 10/2011 | Holaday et al. | |
| 2011/0275820 A1 | 11/2011 | Dlubaia et al. | |
| 2012/0270847 A1 | 10/2012 | Franklin et al. | |
| 2013/0210808 A1 | 8/2013 | Maelicke | |
| 2014/0371255 A1 | 12/2014 | Zhang et al. | |
| 2015/0072005 A1* | 3/2015 | Habboushe | A61K 9/20 424/471 |
| 2016/0200731 A1 | 7/2016 | Mickle et al. | |
| 2016/0338946 A1 | 11/2016 | Shah et al. | |
| 2016/0368931 A1 | 12/2016 | Singh | |
| 2016/0368932 A1 | 12/2016 | Singh | |
| 2017/0014404 A1 | 1/2017 | McKinney et al. | |

(Continued)

FOREIGN PATENT DOCUMENTS

CN 1204649 A 1/1999
CN 103408656 A 11/2013

(Continued)

OTHER PUBLICATIONS

Bennett, D.B., et al., "Biodegradable Polymeric Prodrugs of Naltrexone," Journal of Controlled Release, 16, pp. 43-52 (1991).
Bidlack, J.M., "Pharmalogical Properties of Bivalent Ligands Containing Butorphan Linked to Nalbuphine, Naltrexone, and Naloxone at μ, σ, and κ Opioid Receptors," J. Med. Chem, 50, pp. 2254-2258 (2007).
Bu, Y., "Synthesis and Binding Assay of New Dimeric Ligands Containing the Naltrexone Pharmacophore for mu and kappa Opioid Receptors," Divisional of Medicinal Chemistry, the 229th ACS National Meeting, San Diego, CA, Mar. 13-17, 2005.
Burce, G., et al., "Quantitative Determination of Naltrexone and Naltrexone Prodrugs by Electron-Capture Gas-Liquid Chromatography," Journal of Chromatopgraphy, 137, pp. 323-332 (1977).

(Continued)

*Primary Examiner* — Niloofar Rahmani
(74) *Attorney, Agent, or Firm* — Elmore Patent Law Group, P.C.; Carolyn Elmore; Joseph Zucchero

(57) ABSTRACT

The present invention provides compounds useful for the treatment of opioid dependence, alcohol dependence, alcohol use disorder, or the prevention of relapse to opioid dependence in a subject in need thereof. Related pharmaceutical compositions and methods are also provided herein.

13 Claims, 1 Drawing Sheet

(56) References Cited

U.S. PATENT DOCUMENTS

| | | | |
|---|---|---|---|
| 2017/0020862 A1 | 1/2017 | Brown | |
| 2017/0035709 A1 | 2/2017 | Singh | |

FOREIGN PATENT DOCUMENTS

| | | | |
|---|---|---|---|
| EP | 0071433 A1 | 2/1983 | |
| EP | 0442769 A2 | 8/1991 | |
| EP | 1149836 A1 | 10/2001 | |
| EP | 1422230 A1 | 5/2004 | |
| EP | 1595541 A | 11/2005 | |
| EP | 1603597 B1 | 12/2005 | |
| EP | 2910242 A1 | 8/2015 | |
| FR | 1364228 A | 8/1906 | |
| FR | 2657350 A1 | 7/1991 | |
| JP | 1998048787 | 2/1998 | |
| JP | 2002342688 A | 6/2004 | |
| NO | 2017/053936 A1 | 3/2017 | |
| RU | 2215741 C1 | 11/2003 | |
| WO | 9531463 A1 | 11/1995 | |
| WO | 9616063 A1 | 5/1996 | |
| WO | 9628451 A1 | 9/1996 | |
| WO | 02/098427 A2 | 12/2002 | |
| WO | 2003011881 A2 | 2/2003 | |
| WO | 03/049804 A2 | 6/2003 | |
| WO | 03/051888 A1 | 6/2003 | |
| WO | 03/070191 A1 | 8/2003 | |
| WO | 03/077867 A2 | 9/2003 | |
| WO | 2004/005294 A2 | 1/2004 | |
| WO | 2004/064839 A1 | 8/2004 | |
| WO | 2004/082620 A2 | 9/2004 | |
| WO | 2005/009377 A2 | 2/2005 | |
| WO | 2006/135650 A1 | 12/2006 | |
| WO | 2007/022535 A2 | 2/2007 | |
| WO | 2007/120864 A2 | 10/2007 | |
| WO | 2007/140272 A2 | 12/2007 | |
| WO | 2006/019115 A2 | 2/2008 | |
| WO | 2008/030567 A2 | 3/2008 | |
| WO | 2008/070149 A2 | 6/2008 | |
| WO | 2008/101187 A2 | 8/2008 | |
| WO | 2009/092071 A2 | 7/2009 | |
| WO | 2009/092073 A2 | 7/2009 | |
| WO | 2009/099411 A1 | 8/2009 | |
| WO | 2009/120889 A2 | 10/2009 | |
| WO | 2009/132313 A2 | 10/2009 | |
| WO | 2010/067007 A2 | 6/2010 | |
| WO | 2010/083384 A2 | 7/2010 | |
| WO | 2010/112942 A1 | 10/2010 | |
| WO | 2011/007247 A1 | 1/2011 | |
| WO | 2011031350 A1 | 3/2011 | |
| WO | 2011083304 A1 | 7/2011 | |
| WO | 2011123863 A1 | 10/2011 | |
| WO | 2011123866 A1 | 10/2011 | |
| WO | 2012088441 A1 | 6/2012 | |
| WO | 2012109445 A1 | 8/2012 | |
| WO | 2013093931 A2 | 6/2013 | |
| WO | 2013/106528 A1 | 7/2013 | |
| WO | 2015/082932 A1 | 6/2015 | |
| WO | 2015/168014 A1 | 11/2015 | |
| WO | 2016/014864 A1 | 1/2016 | |
| WO | 2016/189393 A1 | 12/2016 | |
| WO | 2017/033208 A2 | 3/2017 | |
| WO | 2017/053938 A1 | 3/2017 | |
| WO | 2017/091827 A1 | 6/2017 | |

OTHER PUBLICATIONS

Comer, S.D., et al., "Depot Naltrexone: Long-Lasting Antagonism of the Effects of Heroin in Humans," Psychopharmacology, 159, pp. 351-360 (2002).

Dasher, W., et al., "Electrophilic Opioid Ligands. Oxygen Tethered α-Methylene-γ-lactone, Acrylate, Isothiocyanate, and Epoxide Derivatives of 6β-Naltrexol;" American Chemical Society, vol. 35, No. 13, pp. 2374-2384 (1992).

deGroot, F., et al.; "Elongated Multiple Electronic Cascade and Cyclization Spacer Systems in Activatible Anticancer Prodrugs for Enhanced Drug Release," J. Org. Chem., 66, pp. 8815-8830 (2001).

Decker, M,, et al., "Univalent and Bivalent Ligands of Butorphan: Characteristics of the Linking Chain Determine the Affinity and Potency of Such Opioid Ligands," J. Med. Chem., 52, pp. 7389-7396 (2009).

Delaney, E., et al., "Alternative Diaspirins for Modification of Hemoglobin and Sickle Hemoglobin," Archives of Biochemistry and Biophysics, vol. 228, No. 2, pp. 627-638 (1984).

Eldridge, J., "Synthesis and Stability Studies of Prodrugs and Codrugs of Naltrexone and 6-β-Naltrexol," Theses and Dissertations-Pharmacy, University of Kentucky (2013).

Férriz, J,M., et al,, "Prodrug Design of Phenolic Drugs," Current Pharmaceutical Design, 16, pp. 2033-2052 (2010).

Galloway, G., et al., "Pharmacokinetics, Safety, and Tolerability of a Depot Formulation of Naltrexone in Alcoholics: An Open-Label Trial," BMC Psychiatry, vol. 5:18, pp. 1-10 (2005).

Hahn, E., et al., "Irreversible Opiate Agonists and Antagonists: II. Evidence Against a Bivalent Mechanism of Action for Opia839-te Azines and Diacylhydrazones," The Journal of Pharmacology and Experimental Therapeutics, vol. 235, No. 3, pp. 839-845 (1985).

Harvey, J., et al., "Tuned-Affinity Bivalent Ligands for the Characterization of Opioid Receptor Heteromers," ACS Publications, 3, pp. 640-644 (2012).

Huang, J-F., et al., "The Effects of Electrically Assisted Methods on Transdermal Delivery of Nalbuphine Benzoate and Sebacoyl Dinalbuphine Ester from Solutions and Hydrogels," International Journal of Pharmaceutics, 297, pp. 162-171 (2005).

Hussain, M,, et al., "Naltrexone-3-Salicylate (a Prodrug of Naltrexone): Synthesis and Pharmacokinetics in Dogs," Pharmaceutical Research, vol. 5, No, 2, pp. 113-115 (1988).

Hussain, M., et al., "Improvement of the Oral Bioavailability of Naltrexone in Dogs: A Prodrug Approach," Journal of Pharmaceutical Sciences, vol. 76, No. 5, May 1987.

Koolpe, G., et al., "Opioid Agonists and Antagonists, 6-Desoxy-6-Substituted Lactone, Epoxide, and Glycidate Ester Derivatives of Naltrexone and Oxymorphone," J. Med, Chem, 28, pp. 949-957 (1985).

Li, G., et al., "14-O-Heterocyciic-Substituted Naltrexone Derivatives as Non-Peptide mu Opioid Receptor Selective Antagonists: Design, Synthesis, and Biological Studies," Bioorganic & Medicinal Chemistry Letters, 19, pp. 1825-1829 (2009).

Mathews, J., et al., "Characterization of a Novel Bivalent Morphinan Possessing K Agonist and μ Agonist/Antagonist Properties," The Journal of Pharmacology and Experimental Therapeutics, vol. 315, No. 2, pp. 821-827 (2006).

Mohamed, M.S., "Opioid Antagonist Bivalent Ligands as Receptor Probes," Bull. Fac. Pharm. Cairo Univ., vol. 29, No. 2 (1991).

Neumeyer, J., "Design and Synthesis of Novel Dimeric Morphinan Ligands for K and μ Opioid Receptors," J. Med. Chem,, vol. 46, pp. 5162-5170 (2003).

Olsen, L. et al,, "Conjugate Addition Ligands of Opioid Antagonists. Methacrylate Esters and Ethers of 6α- and 6β Naltrexol," J. Med. Chem., Vol, 33, pp. 737-741 (1990).

Pao, L., et al., "High-Performance Liquid Chromatographic Method for the Simultaneous Determination of Nalbuphine and Its Prodrug, Sebacoyl Dinalbuphine Ester, in Dog Plasma and Application to Pharmacokinetic Studies in Dogs," Journal of Chromatography, vol. 746, pp. 241-241 (2000).

Pao, L., et al., "In Vitro and In Vivo Evaluation of the Metabolism and Pharmacokinetics of Sebacoyl Dinalbuphine," Drug Metabolism and Disposition, vol. 33, No. 3, pp. 395-402 (2005).

Pertino, M., et al., "Gastroprotective Effect of Carnosic Acid γ-Lactone Derivatives," J. Nat. Prod., vol. 73, pp. 639-643 (2010).

Pillai, O., et al., "Physicochemical Evaluation, in Vitro Human Skin Diffusion, and Concurrent Biotransformation of 3-O-Alkyl Carbonate Prodrugs of Naltrexone," Pharmaceutical Research, vol. 21, No. 7, pp. 1146-1152 (Jul. 2004).

Remenar, J., "Making the Leap from Daily Oral Dosing to Long-Acting Injectables: Lessons from the Antipsychotics," Molecular Pharmaceutics, vol. 11, pp. 1739-1749 (2014).

(56) References Cited

OTHER PUBLICATIONS

Simon, C., et al., "Stereoselective Synthesis of β-Naltrexol, β-Naloxoi, β-Naloxamine, β-Naltrexamine and Related Compounds by the Application of the Mitsunobu Reaction," Tetrahedron, vol. 50, No. 32, pp. 9757-9768 (1994).

Trécant, C., et al., "New Approach in the Synthesis of M6G," Tetrahedron Letters, vol. 52, pp. 4753-4755 (2011).

Vaddi, H., et al., Human Skin Permeating of 3-O-Alkyl Carbarnate Prodrugs of Naltrexone, Journal of Pharmaceutical Sciences, vol. 98, No. 8, pp. 2611-2625 (Aug. 2009).

Valiveti, S., et al., "In Vivo Evaluation of 3-O-Alkyl Ester Transdermal Prodrugs of Naltrexone in Hairless Guinea Pigs," Journal of Controlled Release, 102, pp. 509-520 (2005).

Vivitrol, Highlights of Prescribing Information, Alkermes, 2015.

Yeh, C., et al., "Sebacoyl Dinalbuphine Ester Extended-Release Injection for Long-Acting Analgesia: A Multicenter, Randomized, Double Blind, and Placebo-controlled study in Hemorrhoidectomy Patients," The Clinical Journal of Pain, Wolters Kluwer Health (2016).

Yuan, Y., "Design, Synthesis, and Biological Evaluation of 14-Heteroaromatic-Substituted Naltrexone Derivatives: Pharmacological Profile Switch from Mu Opioid Receptor Selectivity to Mu/Kappa Opioid Receptor Dual Selectivity," Journal of Medicinal Chemistry, vol. 56, pp. 9156-9169 (2013).

Zhang, B., et al., "Synthesis and binding affinity of novel mono- and bivalent morphinan ligands for κ, μ, and σ opioid receptors," Bioorganic & Medicinal Chemistry, vol. 19, pp. 2808-2816 (2011).

Archer, S., et al.,"14a,14'@.)-[D it hiobis[ (2-oxo-2,1-eth anediyl)imino]]bis( 7,8-dihydrornorph inone) and 14a,1 4'/3- [ Dit hiobis [ (2-oxo-2,1- eth anediyl)iminol ]b is [7 ,8-dihydro-N-( cyclopropylmethy1) normorphinonel: Chemistry and Opioid Binding Properties," J. Med. Chem, vol. 37, pp. 1578-1585 (1994).

Archer, S., et al., "Suppression of Morphine and Cocaine Self-Administration in Rats by a Mixed Mu Antagonist-Kappa Agonist (N-CMB-TAMO) and a Long-Acting Selective D1 Antagonist (AAS-300)," Bioorganic & Medicinal Chemistry Letters, vol. 6, No. 10, pp. 1139-1144 (1996).

Hamad; M., et al., "Synthesis and hydrolytic behavior of two novel tripartate codrugs of naltrexone and 6β-naltrexol with hydroxybupropion as potential alcohol abuse and smoking cessation agents," Bioorganic & Medicinal Chemistry, vol. 14, pp. 7051-7061 (2006).

Hammell, D., et al., "A Duplex "Gemini" Prodrug of Naltrexone for Transdermal Delivery," Journal of Controlled Release, vol. 97, pp. 283-290 (2004).

Jiang, Q., et al., "Preventing Morphine Antinociceptive Tolerance by Irreversible Mu Opioid Antagonists Before the Onset of Their Antagonism," the Journal of Pharmacology and Experimental Therapeutics, vol. 273, No. 2 (1995).

Xu, J.Y., "N-Cyclobutylrnethyl Analog of Normorphinone, N-CBM-TAMO: A Short-Term Opioid Agonist and Long-Term Mu-Selective Irreversible Opioid Antagonist," The Journal of Pharmacology and Experimental Therapeutics, vol. 279, No. 2, 1996.

STN Search Results, Feb. 21, 2017.
STN Search Results, Jun. 12, 2017.
STN Search Results, Feb. 21, 2018.
STN Search Results, Feb. 6, 2018.

\* cited by examiner

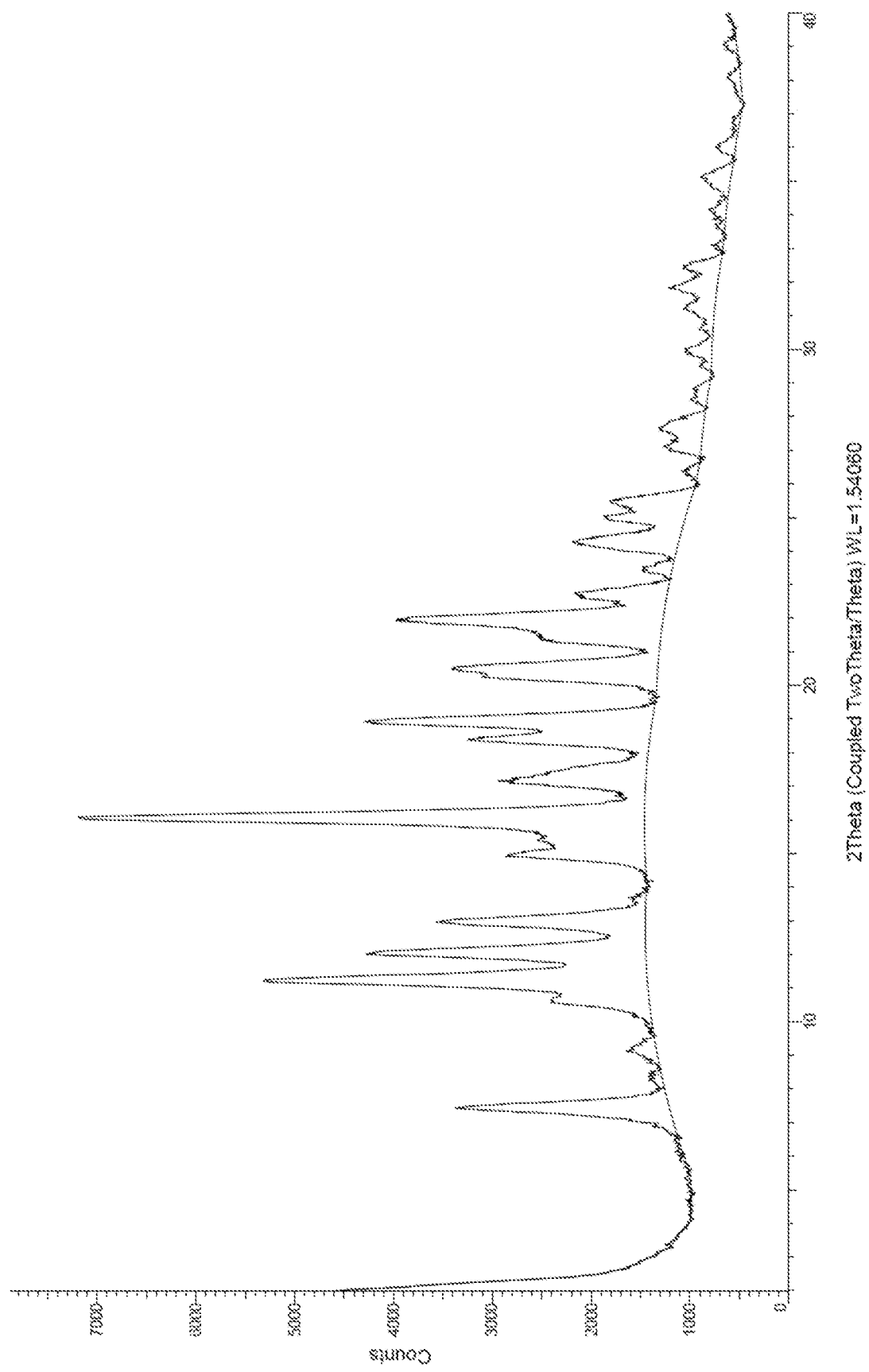

THIENOTHIOPHENE COMPOUNDS FOR LONG-ACTING INJECTABLE COMPOSITIONS AND RELATED METHODS

RELATED APPLICATIONS

This application claims the benefit of U.S. provisional patent application Ser. No. 62/697,899, filed on Jul. 13, 2018 and U.S. provisional patent application Ser. No. 62/699,290, filed on Jul. 17, 2018. The entire teachings of the above applications are incorporated herein by reference.

FIELD OF THE INVENTION

The present invention relates to novel thienothiophene-containing compounds and their use in long-acting injectable compositions. In particular, dimeric prodrugs of naltrexone are disclosed herein. The invention also relates to methods of use thereof.

BACKGROUND OF THE INVENTION

Opioid dependence and alcohol dependence are chronic disorders that result from a variety of genetic, psychological and environmental factors. Traditional treatment has consisted of two phases: detoxification and rehabilitation. Detoxification ameliorates the symptoms and signs of withdrawal while rehabilitation helps the patient avoid future problems with opioids or alcohol. In the past, many rehabilitative treatments have been psychosocial. More recently, there has been increasing interest in medication-assisted treatment. The successful treatment of opioid dependence or alcohol dependence has many serious challenges and complications. Patient compliance can be a particularly difficult challenge to overcome. Accordingly, there is a need for novel and improved therapies.

SUMMARY OF THE INVENTION

The compounds and methods described herein comprise one or more prodrugs of naltrexone. Upon administration, the compounds of the invention can be converted in vivo to naltrexone. Following conversion, the active moiety (i.e., naltrexone) is effective in treating subjects suffering from opioid dependence or alcohol dependence or at risk of developing opioid dependence or alcohol dependence.

The invention provides prodrugs of naltrexone (NTX) having one or two molecules of naltrexone covalently bound to a thienothiophene-containing moiety. The compounds of the invention may extend the period during which the naltrexone is released and absorbed after administration to the subject, providing a longer duration of release than other commercially available naltrexone products, such as VIVITROL® (naltrexone for extended-release injectable suspension) or REVIA® (naltrexone hydrochloride tablets USP).

Provided herein are compounds useful for the prevention or treatment of opioid dependence or alcohol dependence in a subject in need thereof.

In an aspect, provided herein is a compound of Formula I:

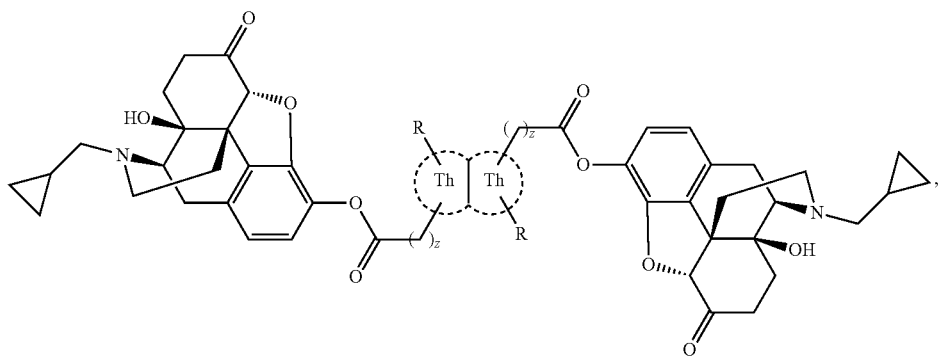

(I)

or a pharmaceutically acceptable salt thereof; wherein:

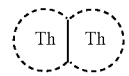

is

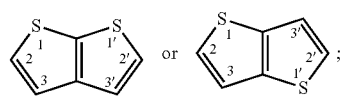

both R groups, always being the same, are selected from hydrogen, halogen, or unsubstituted $C_1$-$C_4$ alkyl;

both values of z, always being the same, are 1, 2, 3, or 4;

wherein the —$(CH_2)_zC(\!\!=\!\!O)O$-naltrexone moieties are bound with points of attachment selected from the 2 and 2' positions or the 3 and 3' positions; and further wherein the R groups are bound with points of attachment as follows:

when the —$(CH_2)_zC(\!\!=\!\!O)O$-naltrexone moieties are bound at the 2 and 2' positions, then the R groups are bound at the 3 and 3' positions; or when the —(CH$_2$)$_z$C(=O)O-naltrexone moieties are bound at the 3 and 3' positions, then the R groups are bound at the 2 and 2' positions.

Examples of a compound of Formula I provided herein include a compound of Formula Ia, Ib, Ic, or Id, or a pharmaceutically acceptable salt thereof.

In another aspect, provided herein is a compound of Formula II:

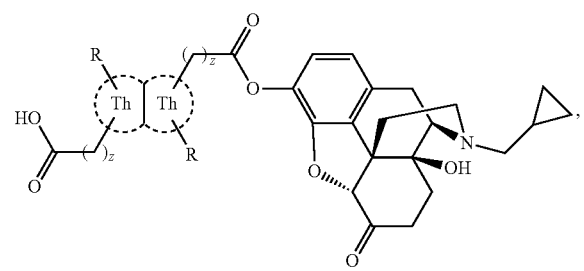

(II)

or a pharmaceutically acceptable salt thereof;
wherein:

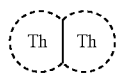

is

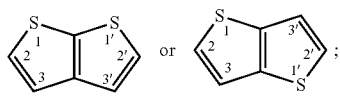

both R groups, always being the same, are selected from hydrogen, halogen, or unsubstituted C$_1$-C$_4$ alkyl;
both values of z, always being the same, are 1, 2, 3, or 4;
wherein the —(CH$_2$)$_z$C(=O)OH moiety and the —(CH$_2$)$_z$ C(=O)O-naltrexone moiety are bound with points of attachment selected from the 2 and 2' positions or the 3 and 3' positions; and
further wherein the R groups are bound with points of attachment as follows:
when the —(CH$_2$)$_z$C(=O)OH moiety and the —(CH$_2$)$_z$C(=O)O-naltrexone moiety are bound at the 2 and 2' positions, then the R groups are bound at the 3 and 3' positions; or
when the —(CH$_2$)$_z$C(=O)OH moiety and the —(CH$_2$)$_z$C(=O)O-naltrexone moiety are bound at the 3 and 3' positions, then the R groups are bound at the 2 and 2' positions.

Examples of a compound of Formula II provided herein include a compound of Formula IIa, IIb, IIc, or IId, or a pharmaceutically acceptable salt thereof.

Also provided herein is a pharmaceutical composition comprising a compound of Formula I or II, or a pharmaceutically acceptable salt thereof, and a pharmaceutically acceptable carrier.

Also provided herein is a method of treating opioid dependence in a subject in need thereof comprising administering to the subject a compound of Formula I or II, or a pharmaceutically acceptable salt thereof. In an embodiment, the opioid is an opioid agonist. In an embodiment, the opioid is morphine, fentanyl, oxymorphone, buprenorphine, hydromorphone, oxycodone, hydrocodone, diamorphine (i.e., heroin) or the like. In another embodiment, the opioid is oxycodone or diamorphine. In another embodiment, the opioid is buprenorphine.

Also provided herein is a method of treating alcohol dependence in a subject in need thereof comprising administering to the subject a compound of Formula I or II, or a pharmaceutically acceptable salt thereof.

Also provided herein is a method of preventing opioid dependence in a subject in need thereof comprising administering to the subject a compound of Formula I or II, or a pharmaceutically acceptable salt thereof. In an embodiment, the opioid is an opioid agonist. In an embodiment, the opioid is morphine, fentanyl, oxymorphone, buprenorphine, hydromorphone, oxycodone, hydrocodone, diamorphine (i.e., heroin) or the like. In another embodiment, the opioid is oxycodone or diamorphine. In another embodiment, the opioid is buprenorphine.

Also provided herein is a method of preventing relapse to opioid dependence in a subject in need thereof comprising administering to the subject a compound of Formula I or II, or a pharmaceutically acceptable salt thereof. In an embodiment, the opioid is an opioid agonist. In an embodiment, the opioid is morphine, fentanyl, oxymorphone, buprenorphine, hydromorphone, oxycodone, hydrocodone, diamorphine (i.e., heroin) or the like. In another embodiment, the opioid is oxycodone or diamorphine. In another embodiment, the opioid is buprenorphine.

Also provided herein is a method of preventing alcohol dependence in a subject in need thereof comprising administering to the subject a compound of Formula I or II, or a pharmaceutically acceptable salt thereof.

Also provided herein is a method of treating alcohol use disorder in a subject in need thereof comprising administering to the subject a compound of Formula I or II, or a pharmaceutically acceptable salt thereof. In another embodiment, the alcohol use disorder is moderate to severe alcohol use disorder.

Also provided herein is a method for the blockade of the effects of exogenously administered opioids in a subject in need thereof comprising administering to the subject a compound of Formula I or II, or a pharmaceutically acceptable salt thereof. In an embodiment, the opioid is an opioid agonist. In an embodiment, the opioid is morphine, fentanyl, oxymorphone, buprenorphine, hydromorphone, oxycodone, hydrocodone, diamorphine (i.e., heroin) or the like. In another embodiment, the opioid is oxycodone or diamorphine. In another embodiment, the opioid is buprenorphine.

BRIEF DESCRIPTION OF THE DRAWINGS

FIG. 1 shows the powder x-ray diffraction (PXRD) pattern for Compound 3.

DETAILED DESCRIPTION OF THE INVENTION

One of the challenges for delivering an active pharmaceutical ingredient (API) in a long-acting injectable composition is incorporating a sufficient amount of drug to maintain effective plasma levels of API over an extended period of time (e.g., several weeks or months) while maintaining a total composition volume that can be readily injected, in a single injection, into a subject. This challenge becomes still more difficult when the API is in the form of a prodrug, and thus having a molecular weight higher than the parent API.

Further, the physicochemical properties of such a prodrug (including, but not limited to, chemical stability, physical stability, physical form and solubility) are important to its suitability for a long-acting injectable composition.

Such long-acting injectable compositions can be in the form of a suspension of solids in an aqueous (liquid) composition. For example, a suspension of a prodrug of an API in an aqueous composition can be prepared for a long-acting composition. In such a system, the physicochemical properties of the prodrug, including crystallinity and solubility of the solid material, are important to its ability to deliver drug over an extended duration and with a therapeutic plasma concentration. In particular, crystalline prodrugs with low aqueous solubility are important for long-acting injectable suspensions.

Provided herein are novel compounds which are prodrugs of naltrexone (NTX) having one or two covalently-attached naltrexone molecules, related methods of treating or preventing opioid dependence or alcohol dependence by administering one or more compounds of the invention, synthetic methods for making the compounds of the invention, and pharmaceutical compositions containing compounds of the invention.

In a non-limiting aspect, the compounds of the present invention may undergo enzyme-mediated cleavage under physiological conditions to release the naltrexone parent drug. In one embodiment, the ultimate release of the naltrexone parent drug is controlled by the rate of dissolution of a crystalline compound of Formula I or II.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±10%, including ±5%, ±1%, and ±0.1% from the specified value, as such variations are appropriate to perform the disclosed methods.

As used herein, "opioid dependence" is generally defined as a chronic brain disease that causes compulsive drug seeking and use.

As used herein, "alcohol dependence" is generally defined as a chronic brain disease that causes compulsive alcohol seeking and use.

As used herein, "alcohol use disorder" is generally defined as encompassing the disorders of alcohol dependence and alcohol abuse and can be classified as mild, moderate or severe.

As used herein, the terms "treat," "treated," "treating," or "treatment" includes the diminishment or alleviation of at least one symptom associated or caused by the state, disorder or disease being treated.

As used herein, the terms "prevent," "preventing," or "prevention" means no disorder or disease development if none had occurred, or no further disorder or disease development if there had already been development of the disorder or disease. Also considered is the ability of one to prevent some or all of the symptoms associated with the disorder or disease.

As used herein, the terms "patient," "individual" or "subject" refer to a human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of a compound of the invention wherein the compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" includes any and all solvents, dispersion media, coatings, antibacterial and antifungal agents, isotonic and absorption delaying agents, and the like, compatible with pharmaceutical administration, such as sterile pyrogen-free water. Suitable carriers are described in Remington's Pharmaceutical Sciences (Genaro, Ed., Mack Publishing Co., 1985, Easton, Pa.), which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the pharmaceutical compositions is contemplated. Supplementary active compounds can also be incorporated into the compositions. The pharmaceutical compositions can also advantageously employ a density enhancing agent, such as a sugar, e.g., mannitol, or sorbitol and/or a tonicity adjusting agent, such as sodium chloride or glycerol. Other pharmaceutical carriers that could be used in the pharmaceutical compositions provided herein also include aqueous methylcellulose solutions, fructose solution, ethanol, or oils of animal, vegetative, or synthetic origin. The pharmaceutically acceptable carrier may also contain preservatives, and buffers as are known in the art.

As used herein, the term "alkyl," by itself or as part of another substituent, means a straight or branched chain hydrocarbon having the number of carbon atoms designated (i.e., $C_1$-$C_4$ alkyl means an alkyl having one to four carbon atoms) and includes straight and branched chains. Examples include methyl, ethyl, propyl, isopropyl, butyl, isobutyl, and tert-butyl.

As used herein, the term "halogen" alone or as part of another substituent means a fluorine, chlorine, bromine, or iodine atom, preferably, fluorine, chlorine, or bromine, more preferably, fluorine or chlorine.

Compounds of the Invention

In one embodiment, a compound of the invention has the structure of Formula I:

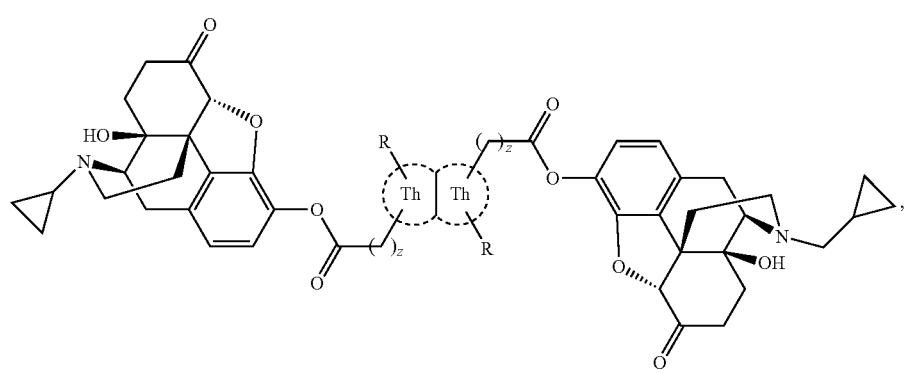

or a pharmaceutically acceptable salt thereof;
wherein:

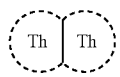

is

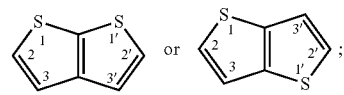

both R groups, always being the same, are selected from hydrogen, halogen, or unsubstituted $C_1$-$C_4$ alkyl;

both values of z, always being the same, are 1, 2, 3, or 4;

wherein the —$(CH_2)_zC(=O)O$-naltrexone moieties are bound with points of attachment selected from the 2 and 2' positions or the 3 and 3' positions; and further wherein the R groups are bound with points of attachment as follows:

when the —$(CH_2)_zC(=O)O$-naltrexone moieties are bound at the 2 and 2' positions, then the R groups are bound at the 3 and 3' positions; or when the —$(CH_2)_zC(=O)O$-naltrexone moieties are bound at the 3 and 3' positions, then the R groups are bound at the 2 and 2' positions.

In another embodiment of Formula I, both R groups are hydrogen.

In another embodiment of Formula I, both R groups are halogen.

In another embodiment of Formula I, both R groups are fluorine.

In another embodiment of Formula I, both R groups are chlorine.

In another embodiment of Formula I, both R groups are unsubstituted $C_1$-$C_4$ alkyl.

In another embodiment of Formula I, both R groups are unsubstituted $C_1$-$C_2$ alkyl.

In another embodiment of Formula I, both R groups are methyl.

In another embodiment of Formula I, both values of z are 1.

In another embodiment of Formula I, both values of z are 2.

In another embodiment of Formula I, both values of z are 3.

In another embodiment of Formula I, both values of z are 4.

In another embodiment of Formula I, both values of z, always being the same, are 1, 2 or 3.

In another embodiment of Formula I, both values of z, always being the same, are 1 or 2.

In another embodiment of Formula I, both R groups are hydrogen and both values of z are 1.

In another embodiment of Formula I, both R groups are hydrogen and both values of z are 2.

In another embodiment of Formula I, both R groups are hydrogen and both values of z are 3.

In another embodiment of Formula I, both R groups are hydrogen and both values of z are 4.

In another embodiment of Formula I, both R groups are halogen and both values of z are 1. For example, both R groups are chlorine. For example, both R groups are fluorine.

In another embodiment of Formula I, both R groups are halogen and both values of z are 2. For example, both R groups are chlorine. For example, both R groups are fluorine.

In another embodiment of Formula I, both R groups are unsubstituted $C_1$-$C_4$ alkyl and both values of z are 1.

In another embodiment of Formula I, both R groups are unsubstituted $C_1$-$C_4$ alkyl and both values of z are 2.

In another embodiment of Formula I, both R groups are unsubstituted $C_1$-$C_2$ alkyl and both values of z are 1.

In another embodiment of Formula I, both R groups are unsubstituted $C_1$-$C_2$ alkyl and both values of z are 2.

In another embodiment of Formula I, both R groups are unsubstituted $C_1$-$C_2$ alkyl and both values of z are 3.

In another embodiment of Formula I, both R groups are unsubstituted $C_1$-$C_2$ alkyl and both values of z are 4.

In another embodiment of Formula I, both R groups are methyl and both values of z are 1.

In another embodiment of Formula I, both R groups are methyl and both values of z are 2.

In another embodiment of Formula I, both R groups are methyl and both values of z are 3.

In another embodiment of Formula I, both R groups are methyl and both values of z are 4.

In another embodiment of Formula I, a compound of Formula Ia has the structure:

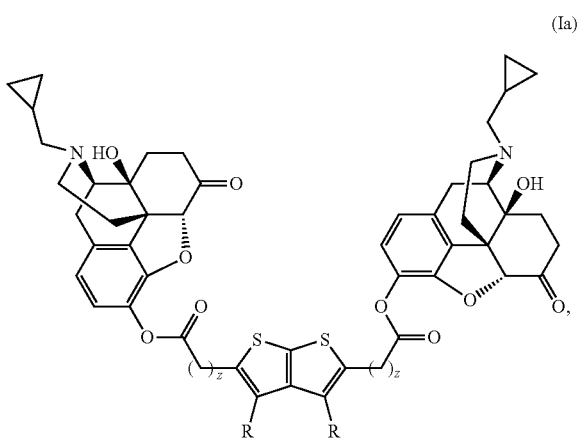

or a pharmaceutically acceptable salt thereof;
wherein:
both R groups, always being the same, are selected from hydrogen, halogen, or unsubstituted $C_1$-$C_4$ alkyl; and
both values of z, always being the same, are 1, 2, 3, or 4.

In another embodiment of Formula Ia, both R groups are hydrogen.

In another embodiment of Formula Ia, both R groups are halogen.

In another embodiment of Formula Ia, both R groups are fluorine.

In another embodiment of Formula Ia, both R groups are chlorine.

In another embodiment of Formula Ia, both R groups are unsubstituted $C_1$-$C_4$ alkyl.

In another embodiment of Formula Ia, both R groups are unsubstituted $C_1$-$C_2$ alkyl.

In another embodiment of Formula Ia, both R groups are methyl.

In another embodiment of Formula Ia, both values of z are 1.

In another embodiment of Formula Ia, both values of z are 2.

In another embodiment of Formula Ia, both values of z are 3.

In another embodiment of Formula Ia, both values of z are 4.

In another embodiment of Formula Ia, both values of z, always being the same, are 1, 2 or 3.

In another embodiment of Formula Ia, both values of z, always being the same, are 1 or 2.

In another embodiment of Formula Ia, both R groups are hydrogen and both values of z are 1.

In another embodiment of Formula Ia, both R groups are hydrogen and both values of z are 2.

In another embodiment of Formula Ia, both R groups are hydrogen and both values of z are 3.

In another embodiment of Formula Ia, both R groups are hydrogen and both values of z are 4.

In another embodiment of Formula Ia, both R groups are halogen and both values of z are 1. For example, both R groups are chlorine. For example, both R groups are fluorine.

In another embodiment of Formula Ia, both R groups are halogen and both values of z are 2. For example, both R groups are chlorine. For example, both R groups are fluorine.

In another embodiment of Formula Ia, both R groups are unsubstituted $C_1$-$C_4$ alkyl and both values of z are 1.

In another embodiment of Formula Ia, both R groups are unsubstituted $C_1$-$C_4$ alkyl and both values of z are 2.

In another embodiment of Formula Ia, both R groups are unsubstituted $C_1$-$C_2$ alkyl and both values of z are 1.

In another embodiment of Formula Ia, both R groups are unsubstituted $C_1$-$C_2$ alkyl and both values of z are 2.

In another embodiment of Formula Ia, both R groups are unsubstituted $C_1$-$C_2$ alkyl and both values of z are 3.

In another embodiment of Formula Ia, both R groups are unsubstituted $C_1$-$C_2$ alkyl and both values of z are 4.

In another embodiment of Formula Ia, both R groups are methyl and both values of z are 1.

In another embodiment of Formula Ia, both R groups are methyl and both values of z are 2.

In another embodiment of Formula Ia, both R groups are methyl and both values of z are 3.

In another embodiment of Formula Ia, both R groups are methyl and both values of z are 4.

In another embodiment of Formula I, a compound of Formula Ib has the structure:

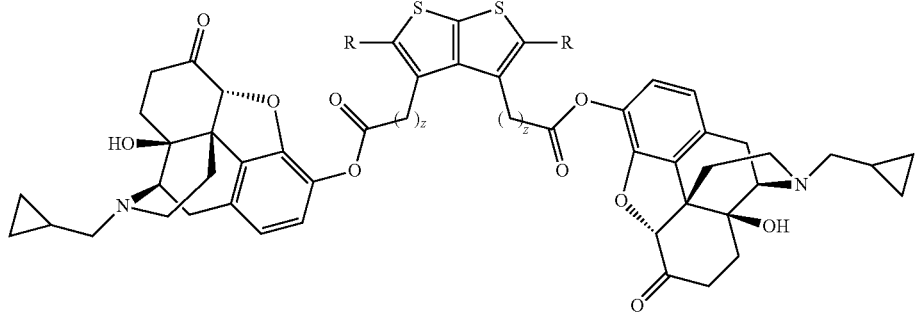
(Ib)

or a pharmaceutically acceptable salt thereof;
wherein:
both R groups, always being the same, are selected from hydrogen, halogen, or unsubstituted $C_1$-$C_4$ alkyl; and
both values of z, always being the same, are 1, 2, 3, or 4.

In another embodiment of Formula Ib, both R groups are hydrogen.

In another embodiment of Formula Ib, both R groups are halogen.

In another embodiment of Formula Ib, both R groups are fluorine.

In another embodiment of Formula Ib, both R groups are chlorine.

In another embodiment of Formula Ib, both R groups are unsubstituted $C_1$-$C_4$ alkyl.

In another embodiment of Formula Ib, both R groups are unsubstituted $C_1$-$C_2$ alkyl.

In another embodiment of Formula Ib, both R groups are methyl.

In another embodiment of Formula Ib, both values of z are 1.

In another embodiment of Formula Ib, both values of z are 2.

In another embodiment of Formula Ib, both values of z are 3.

In another embodiment of Formula Ib, both values of z are 4.

In another embodiment of Formula Ib, both values of z, always being the same, are 1, 2 or 3.

In another embodiment of Formula Ib, both values of z, always being the same, are 1 or 2.

In another embodiment of Formula Ib, both R groups are hydrogen and both values of z are 1.

In another embodiment of Formula Ib, both R groups are hydrogen and both values of z are 2.

In another embodiment of Formula Ib, both R groups are hydrogen and both values of z are 3.

In another embodiment of Formula Ib, both R groups are hydrogen and both values of z are 4.

In another embodiment of Formula Ib, both R groups are halogen and both values of z are 1. For example, both R groups are chlorine. For example, both R groups are fluorine.

In another embodiment of Formula Ib, both R groups are halogen and both values of z are 2. For example, both R groups are chlorine. For example, both R groups are fluorine.

In another embodiment of Formula Ib, both R groups are unsubstituted $C_1$-$C_4$ alkyl and both values of z are 1.

In another embodiment of Formula Ib, both R groups are unsubstituted $C_1$-$C_4$ alkyl and both values of z are 2.

In another embodiment of Formula Ib, both R groups are unsubstituted $C_1$-$C_2$ alkyl and both values of z are 1.

In another embodiment of Formula Ib, both R groups are unsubstituted $C_1$-$C_2$ alkyl and both values of z are 2.

In another embodiment of Formula Ib, both R groups are unsubstituted $C_1$-$C_2$ alkyl and both values of z are 3.

In another embodiment of Formula Ib, both R groups are unsubstituted $C_1$-$C_2$ alkyl and both values of z are 4.

In another embodiment of Formula Ib, both R groups are methyl and both values of z are 1.

In another embodiment of Formula Ib, both R groups are methyl and both values of z are 2.

In another embodiment of Formula Ib, both R groups are methyl and both values of z are 3.

In another embodiment of Formula Ib, both R groups are methyl and both values of z are 4.

In another embodiment of Formula I, a compound of Formula Ic has the structure:

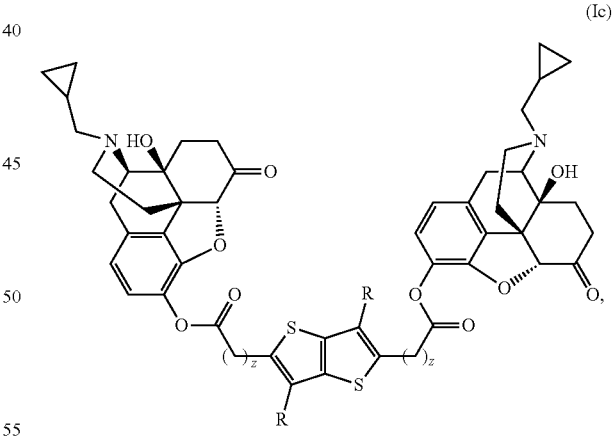
(Ic)

or a pharmaceutically acceptable salt thereof;
wherein:
both R groups, always being the same, are selected from hydrogen, halogen, or unsubstituted $C_1$-$C_4$ alkyl; and
both values of z, always being the same, are 1, 2, 3, or 4.

In another embodiment of Formula Ic, both R groups are hydrogen.

In another embodiment of Formula Ic, both R groups are halogen.

In another embodiment of Formula Ic, both R groups are fluorine.

In another embodiment of Formula Ic, both R groups are chlorine.

In another embodiment of Formula Ic, both R groups are unsubstituted $C_1$-$C_4$ alkyl.

In another embodiment of Formula Ic, both R groups are unsubstituted $C_1$-$C_2$ alkyl.

In another embodiment of Formula Ic, both R groups are methyl.

In another embodiment of Formula Ic, both values of z are 1.

In another embodiment of Formula Ic, both values of z are 2.

In another embodiment of Formula Ic, both values of z are 3.

In another embodiment of Formula Ic, both values of z are 4.

In another embodiment of Formula Ic, both values of z, always being the same, are 1, 2 or 3.

In another embodiment of Formula Ic, both values of z, always being the same, are 1 or 2.

In another embodiment of Formula Ic, both R groups are hydrogen and both values of z are 1.

In another embodiment of Formula Ic, both R groups are hydrogen and both values of z are 2.

In another embodiment of Formula Ic, both R groups are hydrogen and both values of z are 3.

In another embodiment of Formula Ic, both R groups are hydrogen and both values of z are 4.

In another embodiment of Formula Ic, both R groups are halogen and both values of z are 1. For example, both R groups are chlorine. For example, both R groups are fluorine.

In another embodiment of Formula Ic, both R groups are halogen and both values of z are 2. For example, both R groups are chlorine. For example, both R groups are fluorine.

In another embodiment of Formula Ic, both R groups are unsubstituted $C_1$-$C_4$ alkyl and both values of z are 1.

In another embodiment of Formula Ic, both R groups are unsubstituted $C_1$-$C_4$ alkyl and both values of z are 2.

In another embodiment of Formula Ic, both R groups are unsubstituted $C_1$-$C_2$ alkyl and both values of z are 1.

In another embodiment of Formula Ic, both R groups are unsubstituted $C_1$-$C_2$ alkyl and both values of z are 2.

In another embodiment of Formula Ic, both R groups are unsubstituted $C_1$-$C_2$ alkyl and both values of z are 3.

In another embodiment of Formula Ic, both R groups are unsubstituted $C_1$-$C_2$ alkyl and both values of z are 4.

In another embodiment of Formula Ic, both R groups are methyl and both values of z are 1.

In another embodiment of Formula Ic, both R groups are methyl and both values of z are 2.

In another embodiment of Formula Ic, both R groups are methyl and both values of z are 3.

In another embodiment of Formula Ic, both R groups are methyl and both values of z are 4.

In another embodiment of Formula I, a compound of Formula Id has the structure:

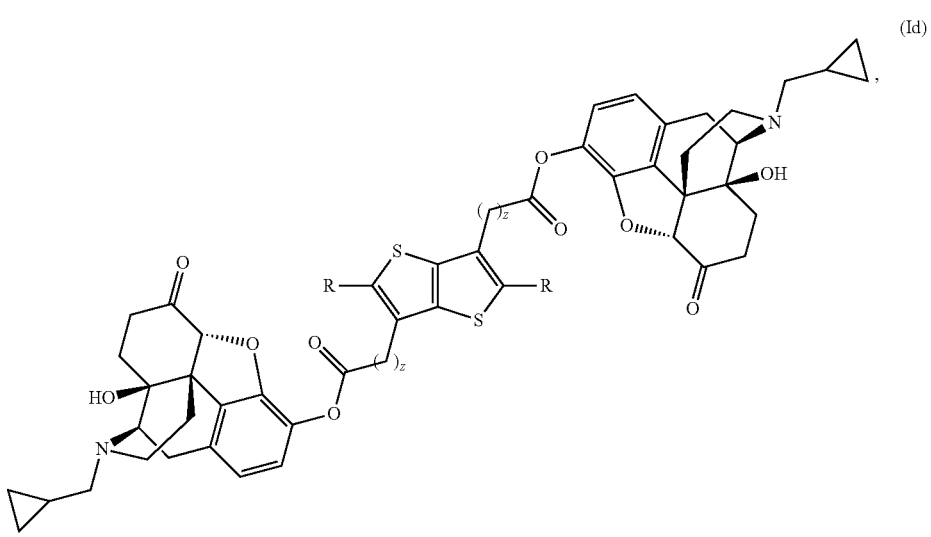

or a pharmaceutically acceptable salt thereof;
wherein:
both R groups, always being the same, are selected from hydrogen, halogen, or unsubstituted $C_1$-$C_4$ alkyl; and
both values of z, always being the same, are 1, 2, 3, or 4.

In another embodiment of Formula Id, both R groups are hydrogen.

In another embodiment of Formula Id, both R groups are halogen.

In another embodiment of Formula Id, both R groups are fluorine.

In another embodiment of Formula Id, both R groups are chlorine.

In another embodiment of Formula Id, both R groups are unsubstituted $C_1$-$C_4$ alkyl.

In another embodiment of Formula Id, both R groups are unsubstituted $C_1$-$C_2$ alkyl.

In another embodiment of Formula Id, both R groups are methyl.

In another embodiment of Formula Id, both values of z are 1.

In another embodiment of Formula Id, both values of z are 2.

In another embodiment of Formula Id, both values of z are 3.

In another embodiment of Formula Id, both values of z are 4.

In another embodiment of Formula Id, both values of z, always being the same, are 1, 2 or 3.

In another embodiment of Formula Id, both values of z, always being the same, are 1 or 2.

In another embodiment of Formula Id, both R groups are hydrogen and both values of z are 1.

In another embodiment of Formula Id, both R groups are hydrogen and both values of z are 2.

In another embodiment of Formula Id, both R groups are hydrogen and both values of z are 3.

In another embodiment of Formula Id, both R groups are hydrogen and both values of z are 4.

In another embodiment of Formula Id, both R groups are halogen and both values of z are 1. For example, both R groups are chlorine. For example, both R groups are fluorine.

In another embodiment of Formula Id, both R groups are halogen and both values of z are 2. For example, both R groups are chlorine. For example, both R groups are fluorine.

In another embodiment of Formula Id, both R groups are unsubstituted $C_1$-$C_4$ alkyl and both values of z are 1.

In another embodiment of Formula Id, both R groups are unsubstituted $C_1$-$C_4$ alkyl and both values of z are 2.

In another embodiment of Formula Id, both R groups are unsubstituted $C_1$-$C_2$ alkyl and both values of z are 1.

In another embodiment of Formula Id, both R groups are unsubstituted $C_1$-$C_2$ alkyl and both values of z are 2.

In another embodiment of Formula Id, both R groups are unsubstituted $C_1$-$C_2$ alkyl and both values of z are 3.

In another embodiment of Formula Id, both R groups are unsubstituted $C_1$-$C_2$ alkyl and both values of z are 4.

In another embodiment of Formula Id, both R groups are methyl and both values of z are 1.

In another embodiment of Formula Id, both R groups are methyl and both values of z are 2.

In another embodiment of Formula Id, both R groups are methyl and both values of z are 3.

In another embodiment of Formula Id, both R groups are methyl and both values of z are 4.

In another embodiment, a compound of the invention has the structure of Formula II:

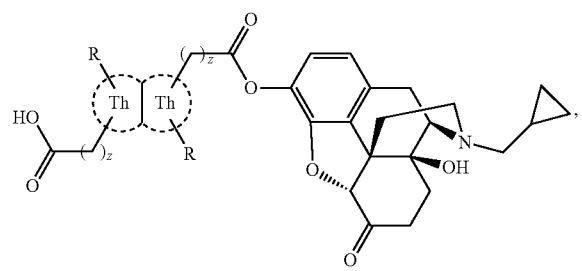

(II)

or a pharmaceutically acceptable salt thereof;
wherein:

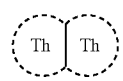

is

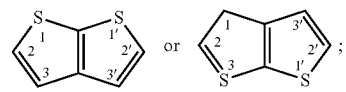

both R groups, always being the same, are selected from hydrogen, halogen, or unsubstituted $C_1$-$C_4$ alkyl;

both values of z, always being the same, are 1, 2, 3, or 4;

wherein the —$(CH_2)_zC(=O)OH$ moiety and the —$(CH_2)_zC(=O)O$-naltrexone moiety are bound with points of attachment selected from the 2 and 2' positions or the 3 and 3' positions; and further wherein the R groups are bound with points of attachment as follows:

when the —$(CH_2)_zC(=O)OH$ moiety and the —$(CH_2)_zC(=O)O$-naltrexone moiety are bound at the 2 and 2' positions, then the R groups are bound at the 3 and 3' positions; or when the —$(CH_2)_zC(=O)OH$ moiety and the —$(CH_2)_zC(=O)O$-naltrexone moiety are bound at the 3 and 3' positions, then the R groups are bound at the 2 and 2' positions.

In another embodiment of Formula II, both R groups are hydrogen.

In another embodiment of Formula II, both R groups are halogen.

In another embodiment of Formula II, both R groups are fluorine.

In another embodiment of Formula II, both R groups are chlorine.

In another embodiment of Formula II, both R groups are unsubstituted $C_1$-$C_4$ alkyl.

In another embodiment of Formula II, both R groups are unsubstituted $C_1$-$C_2$ alkyl.

In another embodiment of Formula II, both R groups are methyl.

In another embodiment of Formula II, both values of z are 1.

In another embodiment of Formula II, both values of z are 2.

In another embodiment of Formula II, both values of z are 3.

In another embodiment of Formula II, both values of z are 4.

In another embodiment of Formula II, both values of z, always being the same, are 1, 2 or 3.

In another embodiment of Formula II, both values of z, always being the same, are 1 or 2.

In another embodiment of Formula II, both R groups are hydrogen and both values of z are 1.

In another embodiment of Formula II, both R groups are hydrogen and both values of z are 2.

In another embodiment of Formula II, both R groups are hydrogen and both values of z are 3.

In another embodiment of Formula II, both R groups are hydrogen and both values of z are 4.

In another embodiment of Formula II, both R groups are halogen and both values of z are 1. For example, both R groups are chlorine. For example, both R groups are fluorine.

In another embodiment of Formula II, both R groups are halogen and both values of z are 2. For example, both R groups are chlorine. For example, both R groups are fluorine.

In another embodiment of Formula II, both R groups are unsubstituted $C_1$-$C_4$ alkyl and both values of z are 1.

In another embodiment of Formula II, both R groups are unsubstituted $C_1$-$C_4$ alkyl and both values of z are 2.

In another embodiment of Formula II, both R groups are unsubstituted $C_1$-$C_2$ alkyl and both values of z are 1.

In another embodiment of Formula II, both R groups are unsubstituted $C_1$-$C_2$ alkyl and both values of z are 2.

In another embodiment of Formula II, both R groups are unsubstituted $C_1$-$C_2$ alkyl and both values of z are 3.

In another embodiment of Formula II, both R groups are unsubstituted $C_1$-$C_2$ alkyl and both values of z are 4.

In another embodiment of Formula II, both R groups are methyl and both values of z are 1.

In another embodiment of Formula II, both R groups are methyl and both values of z are 2.

In another embodiment of Formula II, both R groups are methyl and both values of z are 3.

In another embodiment of Formula II, both R groups are methyl and both values of z are 4.

In another embodiment of Formula II, a compound of Formula IIa has the structure:

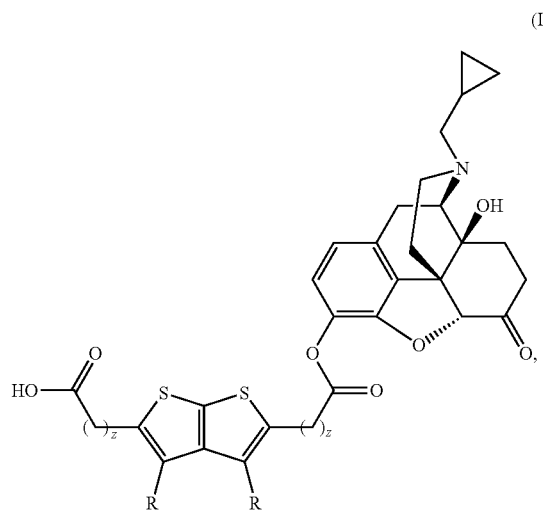

(IIa)

or a pharmaceutically acceptable salt thereof;
wherein:
both R groups, always being the same, are selected from hydrogen, halogen, or unsubstituted $C_1$-$C_4$ alkyl; and
both values of z, always being the same, are 1, 2, 3, or 4.

In another embodiment of Formula IIa, both R groups are hydrogen.

In another embodiment of Formula IIa, both R groups are halogen.

In another embodiment of Formula IIa, both R groups are fluorine.

In another embodiment of Formula IIa, both R groups are chlorine.

In another embodiment of Formula IIa, both R groups are unsubstituted $C_1$-$C_4$ alkyl.

In another embodiment of Formula IIa, both R groups are unsubstituted $C_1$-$C_2$ alkyl.

In another embodiment of Formula IIa, both R groups are methyl.

In another embodiment of Formula IIa, both values of z are 1.

In another embodiment of Formula IIa, both values of z are 2.

In another embodiment of Formula IIa, both values of z are 3.

In another embodiment of Formula IIa, both values of z are 4.

In another embodiment of Formula IIa, both values of z, always being the same, are 1, 2 or 3.

In another embodiment of Formula IIa, both values of z, always being the same, are 1 or 2.

In another embodiment of Formula IIa, both R groups are hydrogen and both values of z are 1.

In another embodiment of Formula IIa, both R groups are hydrogen and both values of z are 2.

In another embodiment of Formula IIa, both R groups are hydrogen and both values of z are 3.

In another embodiment of Formula IIa, both R groups are hydrogen and both values of z are 4.

In another embodiment of Formula IIa, both R groups are halogen and both values of z are 1. For example, both R groups are chlorine. For example, both R groups are fluorine.

In another embodiment of Formula IIa, both R groups are halogen and both values of z are 2. For example, both R groups are chlorine. For example, both R groups are fluorine.

In another embodiment of Formula IIa, both R groups are unsubstituted $C_1$-$C_4$ alkyl and both values of z are 1.

In another embodiment of Formula IIa, both R groups are unsubstituted $C_1$-$C_4$ alkyl and both values of z are 2.

In another embodiment of Formula IIa, both R groups are unsubstituted $C_1$-$C_2$ alkyl and both values of z are 1.

In another embodiment of Formula IIa, both R groups are unsubstituted $C_1$-$C_2$ alkyl and both values of z are 2.

In another embodiment of Formula IIa, both R groups are unsubstituted $C_1$-$C_2$ alkyl and both values of z are 3.

In another embodiment of Formula IIa, both R groups are unsubstituted $C_1$-$C_2$ alkyl and both values of z are 4.

In another embodiment of Formula IIa, both R groups are methyl and both values of z are 1.

In another embodiment of Formula IIa, both R groups are methyl and both values of z are 2.

In another embodiment of Formula IIa, both R groups are methyl and both values of z are 3.

In another embodiment of Formula IIa, both R groups are methyl and both values of z are 4.

In another embodiment of Formula II, a compound of Formula IIb has the structure:

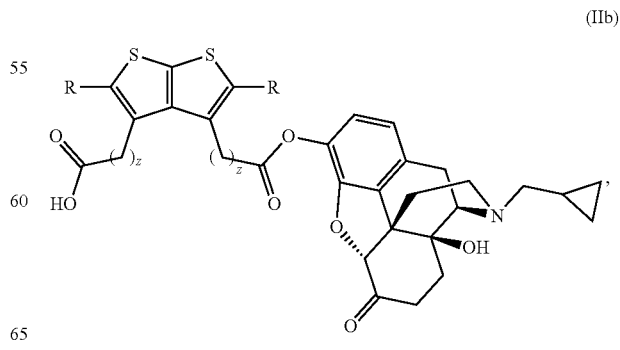

(IIb)

or a pharmaceutically acceptable salt thereof;
wherein:
both R groups, always being the same, are selected from hydrogen, halogen, or unsubstituted $C_1$-$C_4$ alkyl; and
both values of z, always being the same, are 1, 2, 3, or 4.

In another embodiment of Formula IIb, both R groups are hydrogen.

In another embodiment of Formula IIb, both R groups are halogen.

In another embodiment of Formula IIb, both R groups are fluorine.

In another embodiment of Formula IIb, both R groups are chlorine.

In another embodiment of Formula IIb, both R groups are unsubstituted $C_1$-$C_4$ alkyl.

In another embodiment of Formula IIb, both R groups are unsubstituted $C_1$-$C_2$ alkyl.

In another embodiment of Formula IIb, both R groups are methyl.

In another embodiment of Formula IIb, both values of z are 1.

In another embodiment of Formula IIb, both values of z are 2.

In another embodiment of Formula IIb, both values of z are 3.

In another embodiment of Formula IIb, both values of z are 4.

In another embodiment of Formula IIb, both values of z, always being the same, are 1, 2 or 3.

In another embodiment of Formula IIb, both values of z, always being the same, are 1 or 2.

In another embodiment of Formula IIb, both R groups are hydrogen and both values of z are 1.

In another embodiment of Formula IIb, both R groups are hydrogen and both values of z are 2.

In another embodiment of Formula IIb, both R groups are hydrogen and both values of z are 3.

In another embodiment of Formula IIb, both R groups are hydrogen and both values of z are 4.

In another embodiment of Formula IIb, both R groups are halogen and both values of z are 1. For example, both R groups are chlorine. For example, both R groups are fluorine.

In another embodiment of Formula IIb, both R groups are halogen and both values of z are 2. For example, both R groups are chlorine. For example, both R groups are fluorine.

In another embodiment of Formula IIb, both R groups are unsubstituted $C_1$-$C_4$ alkyl and both values of z are 1.

In another embodiment of Formula IIb, both R groups are unsubstituted $C_1$-$C_4$ alkyl and both values of z are 2.

In another embodiment of Formula IIb, both R groups are unsubstituted $C_1$-$C_2$ alkyl and both values of z are 1.

In another embodiment of Formula IIb, both R groups are unsubstituted $C_1$-$C_2$ alkyl and both values of z are 2.

In another embodiment of Formula IIb, both R groups are unsubstituted $C_1$-$C_2$ alkyl and both values of z are 3.

In another embodiment of Formula IIb, both R groups are unsubstituted $C_1$-$C_2$ alkyl and both values of z are 4.

In another embodiment of Formula IIb, both R groups are methyl and both values of z are 1.

In another embodiment of Formula IIb, both R groups are methyl and both values of z are 2.

In another embodiment of Formula IIb, both R groups are methyl and both values of z are 3.

In another embodiment of Formula IIb, both R groups are methyl and both values of z are 4.

In another embodiment of Formula II, a compound of Formula IIc has the structure:

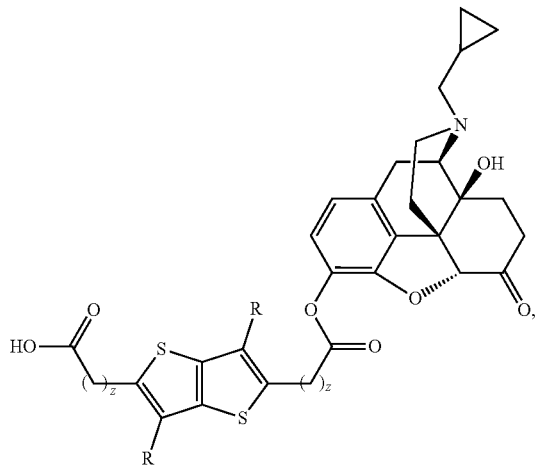

(IIc)

or a pharmaceutically acceptable salt thereof;
wherein:
both R groups, always being the same, are selected from hydrogen, halogen, or unsubstituted $C_1$-$C_4$ alkyl; and
both values of z, always being the same, are 1, 2, 3, or 4.

In another embodiment of Formula IIc, both R groups are hydrogen.

In another embodiment of Formula IIc, both R groups are halogen.

In another embodiment of Formula IIc, both R groups are fluorine.

In another embodiment of Formula IIc, both R groups are chlorine.

In another embodiment of Formula IIc, both R groups are unsubstituted $C_1$-$C_4$ alkyl.

In another embodiment of Formula IIc, both R groups are unsubstituted $C_1$-$C_2$ alkyl.

In another embodiment of Formula IIc, both R groups are methyl.

In another embodiment of Formula IIc, both values of z are 1.

In another embodiment of Formula IIc, both values of z are 2.

In another embodiment of Formula IIc, both values of z are 3.

In another embodiment of Formula IIc, both values of z are 4.

In another embodiment of Formula IIc, both values of z, always being the same, are 1, 2 or 3.

In another embodiment of Formula IIc, both values of z, always being the same, are 1 or 2.

In another embodiment of Formula IIc, both R groups are hydrogen and both values of z are 1.

In another embodiment of Formula IIc, both R groups are hydrogen and both values of z are 2.

In another embodiment of Formula IIc, both R groups are hydrogen and both values of z are 3.

In another embodiment of Formula IIc, both R groups are hydrogen and both values of z are 4.

In another embodiment of Formula IIc, both R groups are halogen and both values of z are 1. For example, both R groups are chlorine. For example, both R groups are fluorine.

In another embodiment of Formula IIc, both R groups are halogen and both values of z are 2. For example, both R groups are chlorine. For example, both R groups are fluorine.

In another embodiment of Formula IIc, both R groups are unsubstituted $C_1$-$C_4$ alkyl and both values of z are 1.

In another embodiment of Formula IIc, both R groups are unsubstituted $C_1$-$C_4$ alkyl and both values of z are 2.

In another embodiment of Formula IIc, both R groups are unsubstituted $C_1$-$C_2$ alkyl and both values of z are 1.

In another embodiment of Formula IIc, both R groups are unsubstituted $C_1$-$C_2$ alkyl and both values of z are 2.

In another embodiment of Formula IIc, both R groups are unsubstituted $C_1$-$C_2$ alkyl and both values of z are 3.

In another embodiment of Formula IIc, both R groups are unsubstituted $C_1$-$C_2$ alkyl and both values of z are 4.

In another embodiment of Formula IIc, both R groups are methyl and both values of z are 1.

In another embodiment of Formula IIc, both R groups are methyl and both values of z are 2.

In another embodiment of Formula IIc, both R groups are methyl and both values of z are 3.

In another embodiment of Formula IIc, both R groups are methyl and both values of z are 4.

In another embodiment of Formula II, a compound of Formula IId has the structure:

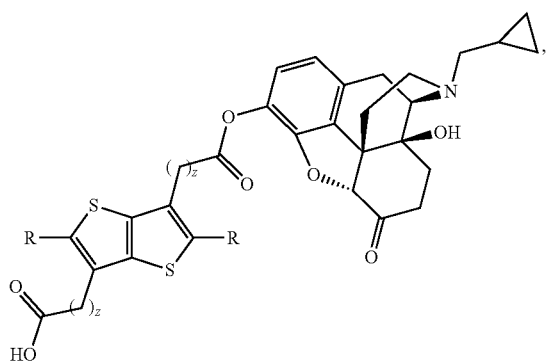

(IId)

or a pharmaceutically acceptable salt thereof;
wherein:
both R groups, always being the same, are selected from hydrogen, halogen, or unsubstituted $C_1$-$C_4$ alkyl; and
both values of z, always being the same, are 1, 2, 3, or 4.

In another embodiment of Formula IId, both R groups are hydrogen.

In another embodiment of Formula IId, both R groups are halogen.

In another embodiment of Formula IId, both R groups are fluorine.

In another embodiment of Formula IId, both R groups are chlorine.

In another embodiment of Formula IId, both R groups are unsubstituted $C_1$-$C_4$ alkyl.

In another embodiment of Formula IId, both R groups are unsubstituted $C_1$-$C_2$ alkyl.

In another embodiment of Formula IId, both R groups are methyl.

In another embodiment of Formula IId, both values of z are 1.

In another embodiment of Formula IId, both values of z are 2.

In another embodiment of Formula IId, both values of z are 3.

In another embodiment of Formula IId, both values of z are 4.

In another embodiment of Formula IId, both values of z, always being the same, are 1, 2 or 3.

In another embodiment of Formula IId, both values of z, always being the same, are 1 or 2.

In another embodiment of Formula IId, both R groups are hydrogen and both values of z are 1.

In another embodiment of Formula IId, both R groups are hydrogen and both values of z are 2.

In another embodiment of Formula IId, both R groups are hydrogen and both values of z are 3.

In another embodiment of Formula IId, both R groups are hydrogen and both values of z are 4.

In another embodiment of Formula IId, both R groups are halogen and both values of z are 1. For example, both R groups are chlorine. For example, both R groups are fluorine.

In another embodiment of Formula IId, both R groups are halogen and both values of z are 2. For example, both R groups are chlorine. For example, both R groups are fluorine.

In another embodiment of Formula IId, both R groups are unsubstituted $C_1$-$C_4$ alkyl and both values of z are 1.

In another embodiment of Formula IId, both R groups are unsubstituted $C_1$-$C_4$ alkyl and both values of z are 2.

In another embodiment of Formula IId, both R groups are unsubstituted $C_1$-$C_2$ alkyl and both values of z are 1.

In another embodiment of Formula IId, both R groups are unsubstituted $C_1$-$C_2$ alkyl and both values of z are 2.

In another embodiment of Formula IId, both R groups are unsubstituted $C_1$-$C_2$ alkyl and both values of z are 3.

In another embodiment of Formula IId, both R groups are unsubstituted $C_1$-$C_2$ alkyl and both values of z are 4.

In another embodiment of Formula IId, both R groups are methyl and both values of z are 1.

In another embodiment of Formula IId, both R groups are methyl and both values of z are 2.

In another embodiment of Formula IId, both R groups are methyl and both values of z are 3.

In another embodiment of Formula IId, both R groups are methyl and both values of z are 4.

The compounds of Formula I are dimeric compounds, each containing two molecules of naltrexone covalently bound to a pro-moiety. Accordingly, in another embodiment, a compound of Formula I, for example a compound of Formula Ia, Ib, Ic or Id, or a pharmaceutically acceptable salt thereof, is administered to a subject and metabolized in vivo to release naltrexone and an intermediate depicted as a compound of Formula II. The resultant compound of Formula II, for example a compound of Formula IIa, IIb, IIc or IId, or a pharmaceutically acceptable salt thereof, may also be metabolized in vivo to release naltrexone. In another embodiment, a compound of Formula II, for example a compound of Formula IIa, IIb, IIc or IId, or a pharmaceutically acceptable salt thereof, is administered to a subject and metabolized in vivo to release naltrexone.

Certain embodiments of compounds of Formula I or II are shown below in Tables A and B, respectively. Compounds of Formulas I or II, or pharmaceutically acceptable salts thereof, and compounds of Tables A and B, are sometimes referred to herein as "compounds of the invention," or "compounds provided herein."

TABLE A

| Compound | Structure |
|---|---|
| 1 | 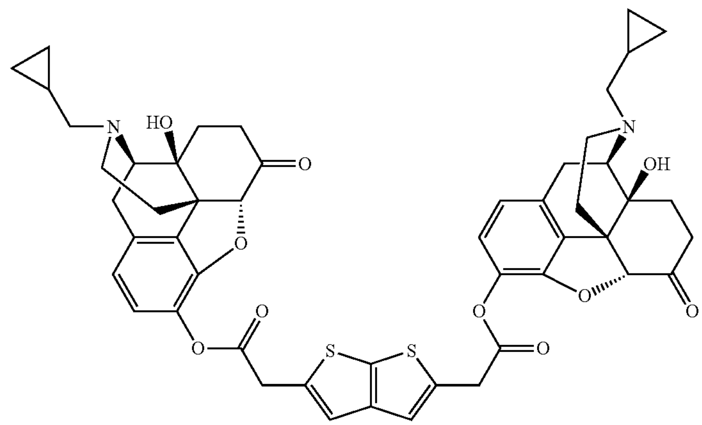 [SMILES: O=C(Cc1cc2cc(CC(=O)Oc3ccc4c5c3O[C@H]3C(=O)CC[C@@]6(O)[C@@H](C4)N(CC4CC4)CC[C@]536)sc2s1)Oc1ccc2c3c1O[C@H]1C(=O)CC[C@@]4(O)[C@@H](C2)N(CC2CC2)CC[C@]314] |
| 2 | 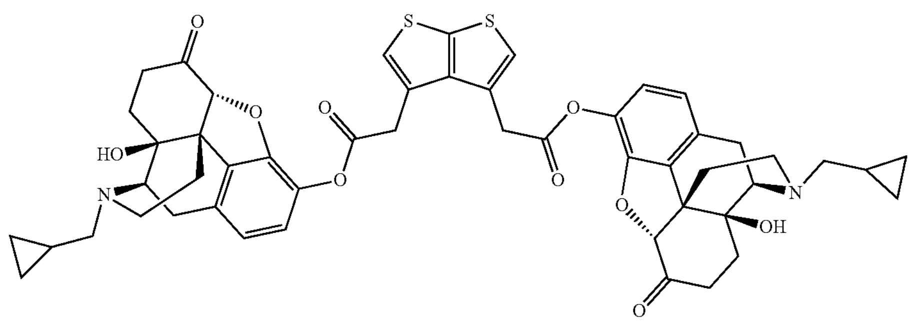 [SMILES: O=C(Cc1csc2scc(CC(=O)Oc3ccc4c5c3O[C@H]3C(=O)CC[C@@]6(O)[C@@H](C4)N(CC4CC4)CC[C@]536)c12)Oc1ccc2c3c1O[C@H]1C(=O)CC[C@@]4(O)[C@@H](C2)N(CC2CC2)CC[C@]314] |
| 3 | 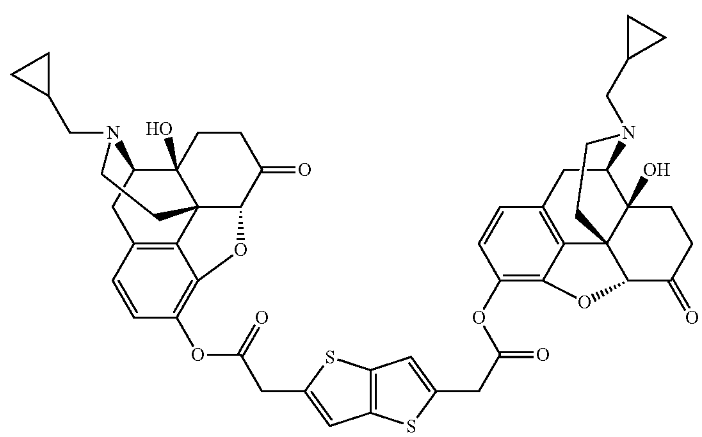 [SMILES: O=C(Cc1cc2sc(CC(=O)Oc3ccc4c5c3O[C@H]3C(=O)CC[C@@]6(O)[C@@H](C4)N(CC4CC4)CC[C@]536)cc2s1)Oc1ccc2c3c1O[C@H]1C(=O)CC[C@@]4(O)[C@@H](C2)N(CC2CC2)CC[C@]314] |

TABLE A-continued

| Compound | Structure |
|---|---|
| 4 | 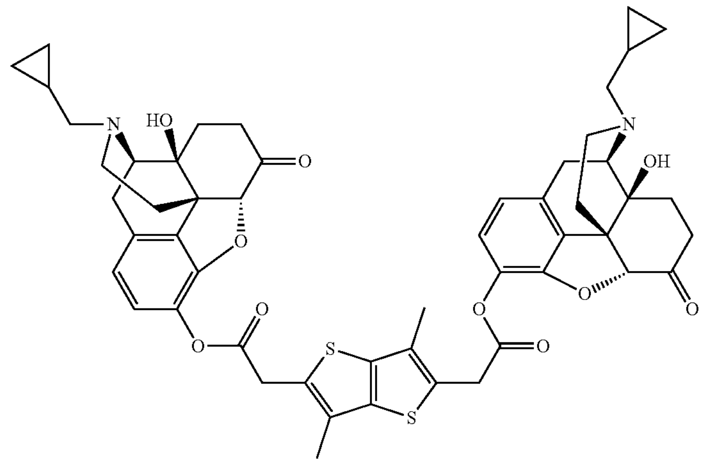 [SMILES: Cc1c(CC(=O)Oc2ccc3c4c2O[C@H]2C(=O)CC[C@@]5(O)[C@@H](C3)N(CC3CC3)CC[C@]425)sc2c(C)c(CC(=O)Oc3ccc4c5c3O[C@H]3C(=O)CC[C@@]6(O)[C@@H](C4)N(CC4CC4)CC[C@]536)sc12] |
| 5 | 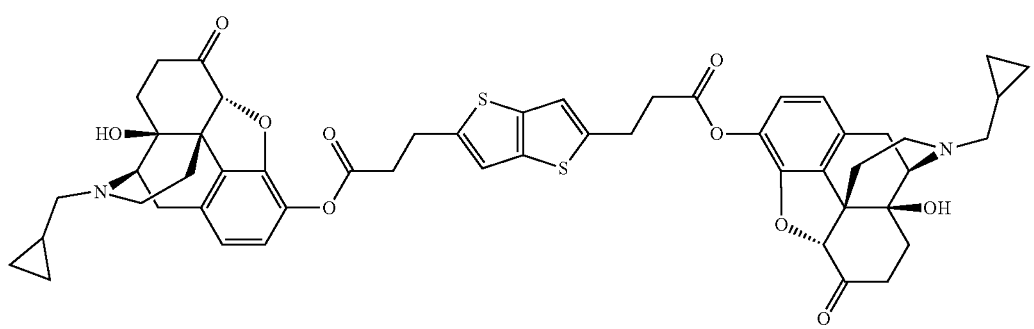 [SMILES: O=C(CCc1cc2sc(CCC(=O)Oc3ccc4c5c3O[C@H]3C(=O)CC[C@@]6(O)[C@@H](C4)N(CC4CC4)CC[C@]536)cc2s1)Oc1ccc2c3c1O[C@H]1C(=O)CC[C@@]4(O)[C@@H](C2)N(CC2CC2)CC[C@]314] |
| 6 | 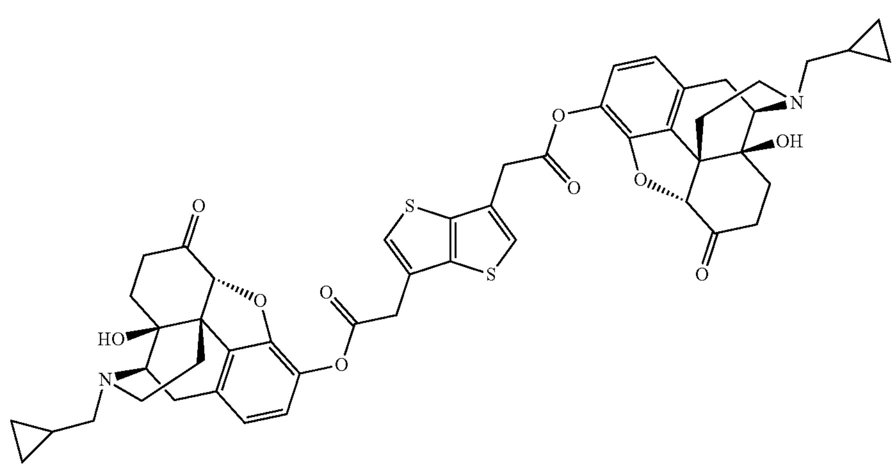 [SMILES: O=C(Cc1csc2c(CC(=O)Oc3ccc4c5c3O[C@H]3C(=O)CC[C@@]6(O)[C@@H](C4)N(CC4CC4)CC[C@]536)csc12)Oc1ccc2c3c1O[C@H]1C(=O)CC[C@@]4(O)[C@@H](C2)N(CC2CC2)CC[C@]314] |

TABLE A-continued
| Compound | Structure |
| --- | --- |
| 7 | 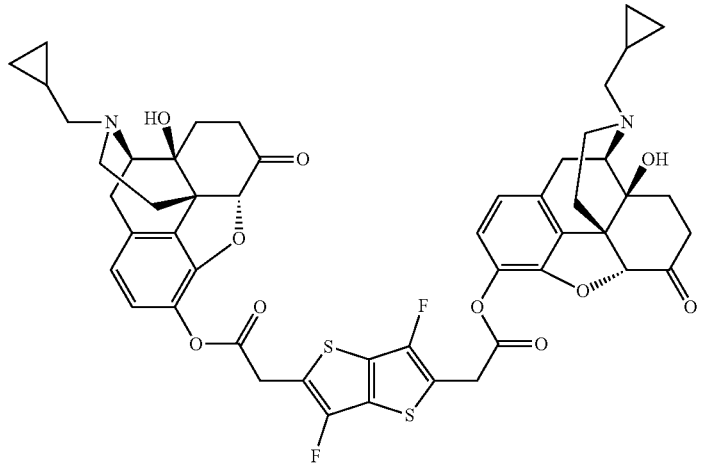 [SMILES: O=C(Cc1sc2c(F)c(CC(=O)Oc3ccc4c5c3O[C@H]3C(=O)CC[C@@]6(O)[C@@H](C4)N(CC4CC4)CC[C@]536)sc2c1F)Oc1ccc2c3c1O[C@H]1C(=O)CC[C@@]4(O)[C@@H](C2)N(CC2CC2)CC[C@]314] |
| 8 | 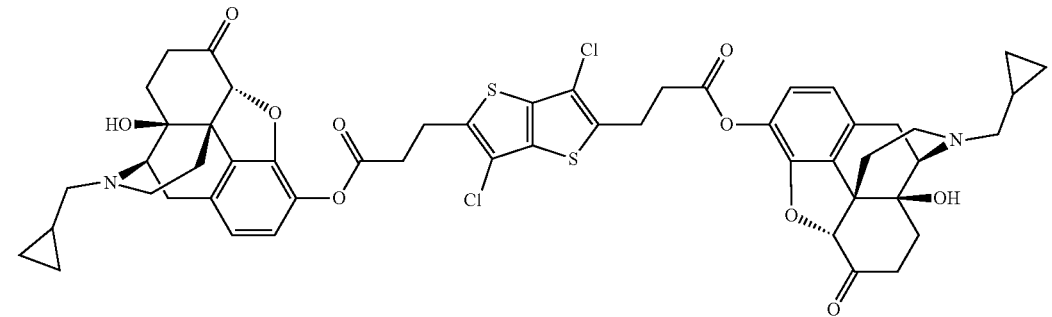 [SMILES: O=C(CCc1sc2c(Cl)c(CCC(=O)Oc3ccc4c5c3O[C@H]3C(=O)CC[C@@]6(O)[C@@H](C4)N(CC4CC4)CC[C@]536)sc2c1Cl)Oc1ccc2c3c1O[C@H]1C(=O)CC[C@@]4(O)[C@@H](C2)N(CC2CC2)CC[C@]314] |
| 9 | 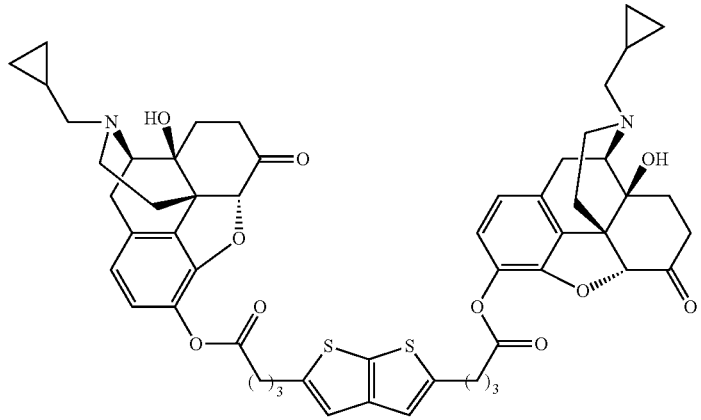 |
| 10 | 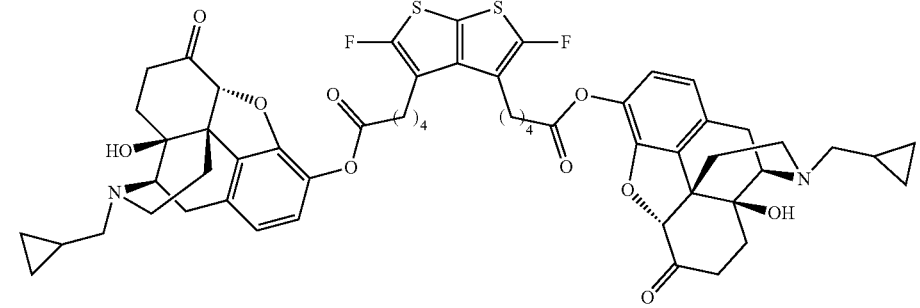 |

TABLE B
| Compound | Structure |
|---|---|
| 1i | 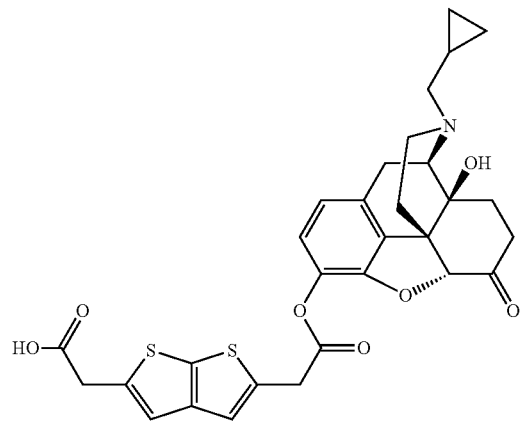 [SMILES: O=C(O)Cc1cc2cc(CC(=O)Oc3ccc4c5c3O[C@H]3C(=O)CC[C@@]6(O)[C@@H](C4)N(CC4CC4)CC[C@]536)sc2s1] |
| 2i | 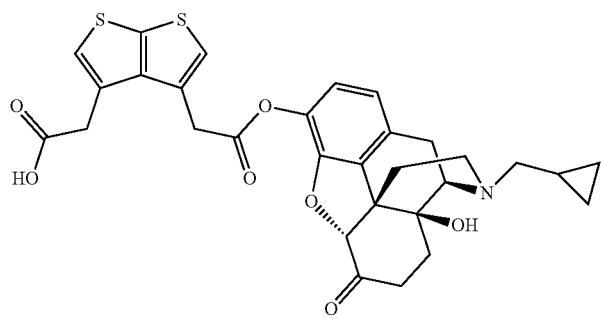 [SMILES: O=C(O)Cc1csc2scc(CC(=O)Oc3ccc4c5c3O[C@H]3C(=O)CC[C@@]6(O)[C@@H](C4)N(CC4CC4)CC[C@]536)c12] |
| 3i | 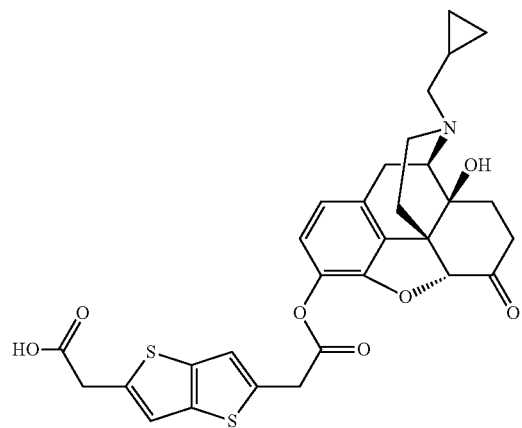 [SMILES: O=C(O)Cc1cc2sc(CC(=O)Oc3ccc4c5c3O[C@H]3C(=O)CC[C@@]6(O)[C@@H](C4)N(CC4CC4)CC[C@]536)cc2s1] |

TABLE B-continued

| Compound | Structure |
|---|---|
| 4i | 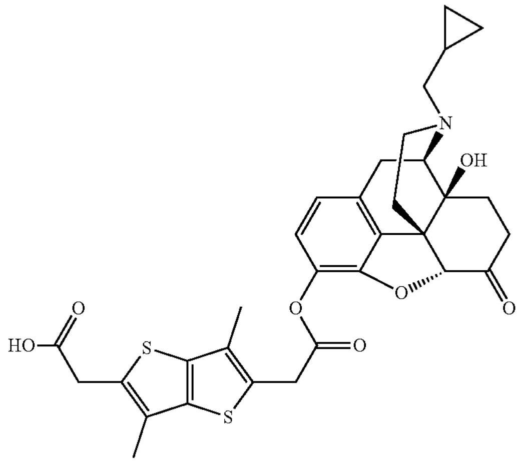 [SMILES: Cc1c(CC(=O)O)sc2c(C)c(CC(=O)Oc3ccc4c5c3O[C@H]3C(=O)CC[C@@]6(O)[C@@H](C4)N(CC4CC4)CC[C@]536)sc12] |
| 5i | 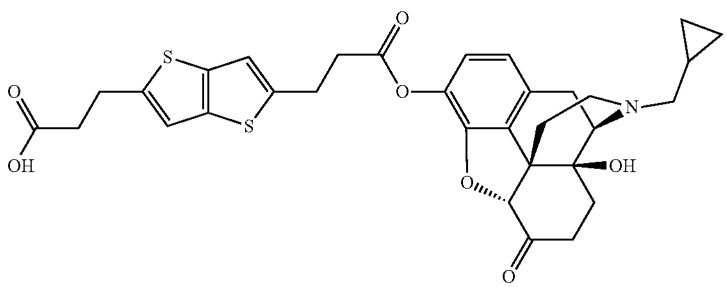 [SMILES: O=C(O)CCc1cc2sc(CCC(=O)Oc3ccc4c5c3O[C@H]3C(=O)CC[C@@]6(O)[C@@H](C4)N(CC4CC4)CC[C@]536)cc2s1] |
| 6i | 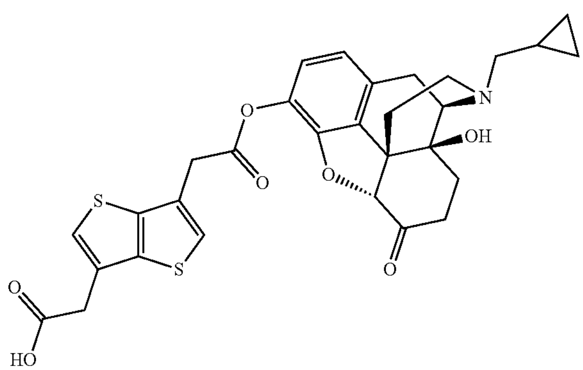 [SMILES: O=C(O)Cc1csc2c(CC(=O)Oc3ccc4c5c3O[C@H]3C(=O)CC[C@@]6(O)[C@@H](C4)N(CC4CC4)CC[C@]536)csc12] |
| 7i | 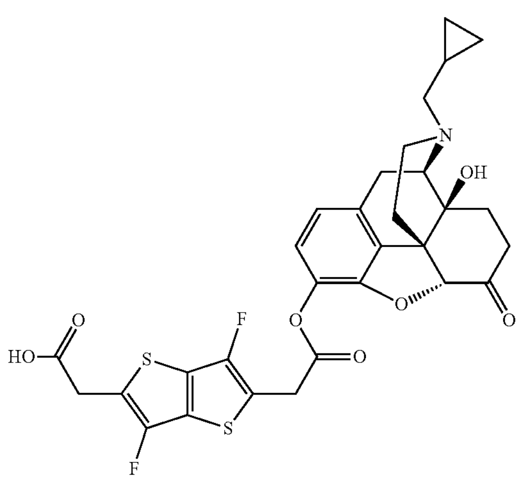 [SMILES: O=C(O)Cc1sc2c(F)c(CC(=O)Oc3ccc4c5c3O[C@H]3C(=O)CC[C@@]6(O)[C@@H](C4)N(CC4CC4)CC[C@]536)sc2c1F] |

TABLE B-continued

| Compound | Structure |
|---|---|
| 8i | (chemical structure) |
| 9i | (chemical structure) |
| 10i | (chemical structure) |

Also provided herein are pharmaceutical compositions comprising a compound of Formula I or II, or a pharmaceutically acceptable salt thereof, and a pharmaceutically acceptable carrier. In one embodiment, the composition is administered to a subject in need of the treatment of opioid dependence. In another embodiment, the composition is administered to a subject in need of the treatment of alcohol dependence. In another embodiment, the composition is administered to a subject in need of the treatment of alcohol use disorder. In another embodiment, the composition is administered to a subject in need of the prevention of opioid dependence. In another embodiment, the composition is administered to a subject in need of the prevention of relapse to opioid dependence. In another embodiment, the composition is administered to a subject in need of the prevention of alcohol dependence.

In any of the compositions or methods as described herein, the compound of Formula I or II, or a pharmaceutically acceptable salt thereof, is present and/or administered in a therapeutically effective amount.

In any of the compositions or methods as described herein, the compound of Formula Ia, Ib, Ic, Id, IIa, IIb, IIc or IId, or a pharmaceutically acceptable salt thereof, is present and/or administered in a therapeutically effective amount.

In another embodiment, a compound of Formula I, or a pharmaceutically acceptable salt thereof, is converted to one equivalent of naltrexone and one equivalent of a compound of Formula II, upon parenteral administration. In another embodiment, a compound of Formula I, or a pharmaceutically acceptable salt thereof, is converted to up to one equivalent of naltrexone and up to one equivalent of a compound of Formula II, upon parenteral administration. In another embodiment, a compound of Formula I, or a pharmaceutically acceptable salt thereof, is converted to from about 0.6 to 0.95 equivalents of naltrexone and a compound of Formula II, upon parenteral administration. In another embodiment, a compound of Formula I, or a pharmaceutically acceptable salt thereof, is converted to from about 0.7 to 0.95 equivalents of naltrexone and a compound of Formula II, upon parenteral administration. In another embodiment, a compound of Formula I, or a pharmaceutically acceptable salt thereof, is converted to from about 0.8 to 0.95 equivalents of naltrexone and a compound of Formula II, upon parenteral administration. For example, about 0.7 equivalents, about 0.75 equivalents, about 0.8 equivalents, about 0.85 equivalents, about 0.9 equivalents, about 0.95 equivalents, or greater than 0.95 equivalents of the total dose of a compound of Formula I, or a pharmaceutically acceptable salt thereof, administered is converted to naltrexone and a compound of Formula II upon parenteral administration. In another embodiment, a compound of Formula I, or a pharmaceutically acceptable salt thereof, is essentially completely converted to naltrexone and a compound of Formula II, upon parenteral administration. In another embodiment, the parenteral administration is via the intramuscular route.

In another embodiment, the resultant compound of Formula II is converted in vivo to one equivalent of naltrexone. In another embodiment, the resultant compound of Formula II is converted in vivo to up to one equivalent of naltrexone. For example, about 0.5 equivalents, about 0.6 equivalents, about 0.7 equivalents, about 0.75 equivalents, about 0.8 equivalents, about 0.85 equivalents, about 0.9 equivalents, about 0.95 equivalents, or greater than 0.95 equivalents of the total amount of a compound of Formula II is converted to naltrexone. In another embodiment, the compound of Formula II is essentially completely converted to naltrexone.

In another embodiment, a compound of Formula I, or a pharmaceutically acceptable salt thereof, may be converted in vivo to two equivalents of naltrexone, upon parenteral administration. In another embodiment, a compound of Formula I, or a pharmaceutically acceptable salt thereof, may be converted to up to two equivalents of naltrexone, upon parenteral administration. For example, about 1.2 equivalents, about 1.3 equivalents, about 1.4 equivalents, about 1.5 equivalents, about 1.6 equivalents, about 1.7 equivalents, about 1.8 equivalents, or greater than 1.8 equivalents of the total dose of a compound of Formula I, or a pharmaceutically acceptable salt thereof, administered is converted to naltrexone, upon parenteral administration. In another embodiment, a compound of Formula I, or a pharmaceutically acceptable salt thereof, is essentially completely converted to naltrexone, upon parenteral administration. In another embodiment, the parenteral administration is via the intramuscular route.

In another embodiment, any one of the compounds 1 to 10 (see Table A), or a pharmaceutically acceptable salt thereof, may be converted in vivo to two equivalents of naltrexone, upon parenteral administration. In another embodiment, any one of the compounds 1 to 10, or a pharmaceutically acceptable salt thereof, may be converted in vivo to up to two equivalents of naltrexone, upon parenteral administration. For example, about 1.2 equivalents, about 1.3 equivalents, about 1.4 equivalents, about 1.5 equivalents, about 1.6 equivalents, about 1.7 equivalents, about 1.8 equivalents, or greater than 1.8 equivalents of the total dose of any one of the compounds 1 to 10, or a pharmaceutically acceptable salt thereof, administered is converted to naltrexone, upon parenteral administration. In another embodiment, any one of the compounds 1 to 10, or a pharmaceutically acceptable salt thereof, is essentially completely converted to naltrexone, upon parenteral administration. In another embodiment, the parenteral administration is via the intramuscular route.

In another embodiment, any one of the compounds 1i to 10i (see Table B) may be converted in vivo to one equivalent of naltrexone. In another embodiment, any one of the compounds 1i to 10i may be converted in vivo to up to one equivalent of naltrexone. For example, about 0.7 equivalents, about 0.75 equivalents, about 0.8 equivalents, about 0.85 equivalents, about 0.9 equivalents, about 0.95 equivalents, or greater than 0.95 equivalents of the total amount of any one of the compounds 1i to 10i is converted to naltrexone. In another embodiment, any one of the compounds 1i to 10i is essentially completely converted to naltrexone.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In another embodiment, the compounds described herein include a $^{2}H$ (i.e., deuterium) isotope. Isotopically-labeled compounds are prepared by any suitable method or by processes using an appropriate isotopically-labeled reagent in place of the non-labeled reagent otherwise employed.

Methods of Treatment

The compounds of the invention can be used in a method of treating a disease or condition in a subject wherein treatment with a compound of the invention would be beneficial, said method comprising administering to the subject a compound of the invention, or a pharmaceutical composition comprising a compound of the invention.

The compounds of the invention can be used to treat a disease or condition selected from the group consisting of opioid dependence or alcohol dependence in a subject in need thereof.

The compounds of the invention can be used to prevent a disease or condition selected from the group consisting of opioid dependence, relapse to opioid dependence, or alcohol dependence in a subject in need thereof.

In one embodiment, the compounds of the invention can be used to treat opioid dependence in a subject in need thereof.

In another embodiment, the compounds of the invention can be used to treat alcohol dependence in a subject in need thereof.

In another embodiment, the compounds of the invention can be used to treat alcohol use disorder in a subject in need thereof.

In yet another embodiment, the compounds of the invention can be used to prevent opioid dependence in a subject in need thereof.

In yet another embodiment, the compounds of the invention can be used to prevent relapse to opioid dependence in a subject in need thereof.

In another embodiment, the compounds of the invention can be used to prevent alcohol dependence in a subject in need thereof.

In another embodiment, the compounds of the invention can be used to treat addiction in a subject in need thereof. The addiction can be drug addiction or alcohol addiction.

The drug addiction can be one or more of opioid addiction (i.e., opioid dependence) or stimulant addiction. The opioid can be one or more of fentanyl, morphine, oxymorphone, buprenorphine, hydromorphone, oxycodone, hydrocodone, or the like. The drug addiction can also be one or more of diamorphine (i.e., heroin), cocaine, nicotine, and amphetamine.

In one embodiment, compounds of the invention can be used to treat a disease or condition in a subject, wherein the subject has a tolerance to opioid medication, the subject has a history of opioid dependency or abuse, the subject is at risk of opioid dependency or abuse, or in circumstances wherein it is desirable that the risk of opioid dependence or opioid addiction in the subject is minimized.

The compounds of the invention can also be used to treat alcohol addiction, which can also be referred to as alcoholism. "Alcoholism" refers to an addictive disease or disorder characterized by an inability to control the intake of alcohol, i.e., a continued excessive or compulsive use of alcoholic drinks. Alcoholism may involve changes an individual's ability to metabolize alcohol as well. Diagnosis of alcoholism can be made by psychiatric examination.

In one aspect, the compounds provided herein are useful in treatment or prevention of opioid dependence or alcohol dependence by being converted in vivo into naltrexone, which acts as an antagonist of the μ-opioid receptor.

In one embodiment of the methods described herein, the subject is human.

Administration/Dosage/Formulations

The compounds of the invention enable compositions with desirable properties and advantages. For example, the compositions can be administered once per month, or once per two months, or once per three months, which is particularly desirable for the subjects described herein. Such compositions can provide many therapeutic benefits that are not achieved with corresponding shorter acting, or immediate-release oral preparations of naltrexone. For example, the composition can maintain lower, more steady plasma concentrations of naltrexone.

In one embodiment, the compound of the invention is administered in a composition suitable for parenteral administration. In another embodiment, the parenteral administration is by injection. In another embodiment, the parenteral administration is by intramuscular injection. Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In one embodiment, a pharmaceutical composition in accordance with the invention may be accomplished by the use of a liquid suspension of crystalline or amorphous material with poor water solubility. In another embodiment, the material is crystalline.

In another embodiment, a pharmaceutical composition may be accomplished by dissolving or suspending the compound of the invention in an oil vehicle.

In another embodiment, a pharmaceutical composition may be accomplished by forming microencapsule matrices of the compound of the invention in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Injectable compositions are also prepared by entrapping the compound in liposomes or microemulsions that are compatible with body tissues.

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the rate of metabolism of the particular compound employed, the rate of clearance of the compound, the duration of the treatment, other drugs, compounds or materials used in combination with the compound, the age, sex, weight, condition, general health and prior medical history of the patient being treated, and like factors well known in the medical arts.

A medical doctor, e.g., physician, having ordinary skill in the art may readily determine and prescribe the effective amount of the pharmaceutical composition required. For example, the physician could begin administration of the pharmaceutical composition to dose a compound of the invention at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of the compound calculated to produce the desired therapeutic effect in association with the required pharmaceutical vehicle. The dosage unit forms of the invention are dictated by and directly dependent on (a) the unique characteristics of the compound and the particular therapeutic effect to be achieved, and (b) the limitations inherent in the art of compounding/formulating such a compound for the treatment or prevention of opioid dependence or alcohol dependence in a subject.

In one embodiment, the compounds of the invention are formulated using one or more pharmaceutically acceptable carriers. In one embodiment, the pharmaceutical compositions of the invention comprise a therapeutically effective amount of a compound of the invention and a pharmaceutically acceptable carrier.

In some embodiments, a single dose of a compound of Formula I or II, or a pharmaceutically acceptable salt thereof, is from about 1 mg to about 5,000 mg. In some embodiments, a single dose of a compound used in compositions described herein is less than about 2,000 mg, or less than about 1,800 mg, or less than about 1,600 mg, or less than about 1,400 mg, or less than about 1,300 mg, or less than about 1,200 mg, or less than about 1,100 mg, or less than about 1,000 mg, or less than about 900 mg, or less than about 800 mg, or less than about 750 mg, or less than about 700 mg, or less than about 600 mg, or less than about 500 mg, or less than about 300 mg or less than about 100 mg. For example, a single dose is about 100 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150 mg, 1,200 mg, 1,250 mg, 1,300 mg, 1,350 mg, 1,400 mg, 1,450 mg, 1,500 mg, 1,550 mg, 1,600 mg, 1,650 mg, 1,700 mg, 1,750 mg, 1,800 mg, 1,850 mg, 1,900 mg 1,950 mg, or about 2,000 mg of a compound of Formula I. In a particular embodiment, the dose is administered as a single parenteral injection. In a specific embodiment, the dose is administered as a single intramuscular injection.

For comparison purposes, VIVITROL® (naltrexone for extended-release injectable suspension) is administered intramuscularly every four weeks or once a month at a dose of 380 mg naltrexone. REVIA® (naltrexone hydrochloride tablets USP) can be administered orally once per day at a dose of 50 mg naltrexone hydrochloride.

In some embodiments, a single intramuscular injection is administered with a dose of a compound of Formula I, or a pharmaceutically acceptable salt thereof, of from about 500 mg to about 2,200 mg. In some embodiments, a single intramuscular injection is administered with a dose of a compound of Formula I, or a pharmaceutically acceptable salt thereof, of from about 750 mg to about 2,000 mg. In some embodiments, a single intramuscular injection is administered with a dose of a compound of Formula I, or a pharmaceutically acceptable salt thereof, of from about 1,000 mg to about 2,000 mg. In some embodiments, a single intramuscular injection is administered with a dose of a compound of Formula I, or a pharmaceutically acceptable salt thereof, of from about 1,200 mg to about 1,800 mg.

In another embodiment, a pharmaceutical composition comprises a compound of Formula I or II or a pharmaceutically acceptable salt thereof, and a pharmaceutically acceptable carrier; wherein the composition provides a duration of release of naltrexone of, from about 1 week to about 15 weeks, following parenteral administration. In another embodiment, the duration of release of naltrexone is from about 2 weeks to about 15 weeks, or from about 4 weeks to about 15 weeks, or from about 6 weeks to about 15 weeks, or from about 8 weeks to about 15 weeks, or from about 8 weeks to about 14 weeks, or from about 8 weeks to about 12 weeks. In another embodiment, the duration of release of naltrexone is about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks. In another embodiment, the duration of release of naltrexone is about 8 weeks. In another embodiment, the duration of release of naltrexone is about 9 weeks. In another embodiment, the duration of release of naltrexone is about 10 weeks. In another embodiment, the duration of release of naltrexone is about 11 weeks. In another embodiment, the duration of release of naltrexone is about 12 weeks. In another embodiment, the duration of release of naltrexone is about 13 weeks. In another embodiment, the duration of release of naltrexone is about 14 weeks. In another embodiment, the duration of release of naltrexone is about 15 weeks. In another embodiment, the duration of release of naltrexone is about 1 month. In another embodiment, the duration of release of naltrexone is about 2 months. In another embodiment, the duration of release of naltrexone is about 3 months. In another embodiment, the parenteral administration is intramuscular administration.

In another embodiment, a pharmaceutical composition comprises a compound of Formula I or II or a pharmaceutically acceptable salt thereof, and a pharmaceutically acceptable carrier; wherein the composition provides a minimum naltrexone blood plasma concentration of, from about 0.5 to about 10 ng/mL, following parenteral administration. In another embodiment, the minimum naltrexone blood plasma concentration is at least from about 0.7 to about 10 ng/mL, or from about 0.8 to about 8.0 ng/mL, or from about 1.0 to about 8.0 ng/mL, or from about 1.0 to about 6.0 ng/mL, or from about 1.5 to about 6.0 ng/mL, or from about 1.5 to about 4.0 ng/mL, or from about 1.5 to about 3.0 ng/mL, or from about 1.5 to about 2.5 ng/mL, or from about 1.5 to about 2.0 ng/mL, or from about 2.0 to about 2.5 ng/mL. In another embodiment, the minimum naltrexone blood plasma concentration is about 0.5 ng/mL, 0.8 ng/mL, 1.0 ng/mL, 1.1 ng/mL, 1.2 ng/mL, 1.3 ng/mL, 1.4 ng/mL, 1.5 ng/mL, 1.6 ng/mL, 1.7 ng/mL, 1.8 ng/mL, 1.9 ng/mL, 2.0 ng/mL, 2.1 ng/mL, 2.2 ng/mL, 2.3 ng/mL. 2.4 ng/mL, or 2.5 ng/mL. In another embodiment, the minimum naltrexone blood plasma concentration is about 1.0 ng/mL. In another embodiment, the minimum naltrexone blood plasma concentration is about 1.5 ng/mL. In another embodiment, the minimum naltrexone blood plasma concentration is about 2.0 ng/mL. In another embodiment, the minimum naltrexone blood plasma concentration is about 2.5 ng/mL. In another embodiment, the minimum naltrexone blood plasma concentration is about 3.0 ng/mL. In another embodiment, the parenteral administration is intramuscular administration.

In other embodiments, a pharmaceutical composition comprises a compound of Formula I or II or a pharmaceutically acceptable salt thereof, and a pharmaceutically acceptable carrier; wherein the composition provides a minimum naltrexone blood plasma concentration of, from about 0.5 to about 3.0 ng/mL, following parenteral administration, for a duration of, from about 1 week to about 15 weeks. In another embodiment, the minimum naltrexone blood plasma concentration is at least from about 0.7 to about 3.0 ng/mL, or from about 0.8 to about 2.5 ng/mL, or from about 1.0 to about 2.5 ng/mL, or from about 1.0 to about 2.0 ng/mL, or from about 1.0 to about 1.5 ng/mL, or from about 1.5 to about 2.5 ng/mL, or from about 1.5 to about 2.0 ng/mL, for a duration of, from about 1 week to about 15 weeks, or from about 2 weeks to about 14 weeks, or from about 4 weeks to about 14 weeks, or from about 6 weeks to about 14 weeks, or from about 8 weeks to about 12 weeks, or from about 10 weeks to about 12 weeks. In another embodiment, the minimum naltrexone blood plasma concentration is about 1.0 ng/mL, 1.1 ng/mL, 1.2 ng/mL, 1.3 ng/mL, 1.4 ng/mL, 1.5 ng/mL, 1.6 ng/mL, 1.7 ng/mL, 1.8 ng/mL, 1.9 ng/mL, 2.0 ng/mL, 2.1 ng/mL, 2.2 ng/mL, 2.3 ng/mL. 2.4 ng/mL, or 2.5 ng/mL, for a duration of about 1 week, 2 weeks, 4 weeks, 6 weeks, 8 weeks, 10 weeks, 12 weeks, or about 14 weeks. In another embodiment, the minimum naltrexone blood plasma concentration is about 1.0 ng/mL for a duration of about 14 weeks. In another embodiment, the minimum naltrexone blood plasma concentration is about 1.5 ng/mL for a duration of about 14 weeks. In another embodiment, the minimum naltrexone blood plasma concentration is about 2.0 ng/mL for a duration of about 14 weeks. In another embodiment, the minimum naltrexone blood plasma concentration is about 2.0 ng/mL for a duration of about 12 weeks. In another embodiment, the minimum naltrexone blood plasma concentration is about 2.0 ng/mL for a duration of about 10 weeks. In another embodiment, the minimum naltrexone blood plasma concentration is about 3.0 ng/mL for a duration of about 10 weeks. In another embodiment, the minimum naltrexone blood plasma concentration is about 3.0 ng/mL for a duration of about 8 weeks. In another embodiment, the parenteral administration is intramuscular administration.

In another embodiment, a pharmaceutical composition comprises any one of the compounds 1 to 10 or a pharmaceutically acceptable salt thereof, and a pharmaceutically acceptable carrier; wherein the composition provides a minimum naltrexone blood plasma concentration of about 1.0 ng/mL, following parenteral administration, for a duration of about 8 weeks.

In another embodiment, a pharmaceutical composition comprises any one of the compounds 1 to 10 or a pharmaceutically acceptable salt thereof, and a pharmaceutically acceptable carrier; wherein the composition provides a minimum naltrexone blood plasma concentration of about 1.5 ng/mL, following parenteral administration, for a duration of about 8 weeks.

In another embodiment, a pharmaceutical composition comprises any one of the compounds 1 to 10 or a pharmaceutically acceptable salt thereof, and a pharmaceutically acceptable carrier; wherein the composition provides a minimum naltrexone blood plasma concentration of about 2.0 ng/mL, following parenteral administration, for a duration of about 8 weeks.

In another embodiment, a pharmaceutical composition comprises any one of the compounds 1 to 10 or a pharmaceutically acceptable salt thereof, and a pharmaceutically acceptable carrier; wherein the composition provides a minimum naltrexone blood plasma concentration of about 1.0 ng/mL, following parenteral administration, for a duration of about 12 weeks.

In another embodiment, a pharmaceutical composition comprises any one of the compounds 1 to 10 or a pharmaceutically acceptable salt thereof, and a pharmaceutically acceptable carrier; wherein the composition provides a minimum naltrexone blood plasma concentration of about 1.5 ng/mL, following parenteral administration, for a duration of about 12 weeks.

In another embodiment, a pharmaceutical composition comprises any one of the compounds 1 to 10 or a pharmaceutically acceptable salt thereof, and a pharmaceutically acceptable carrier; wherein the composition provides a minimum naltrexone blood plasma concentration of about 2.0 ng/mL, following parenteral administration, for a duration of about 12 weeks.

In another embodiment, a pharmaceutical composition comprises Compound 3 or a pharmaceutically acceptable salt thereof, and a pharmaceutically acceptable carrier; wherein the composition provides a minimum naltrexone blood plasma concentration of about 1.0 ng/mL, following parenteral administration, for a duration of about 8 weeks.

In another embodiment, a pharmaceutical composition comprises Compound 3 or a pharmaceutically acceptable salt thereof, and a pharmaceutically acceptable carrier; wherein the composition provides a minimum naltrexone blood plasma concentration of about 1.5 ng/mL, following parenteral administration, for a duration of about 8 weeks.

In another embodiment, a pharmaceutical composition comprises Compound 3 or a pharmaceutically acceptable salt thereof, and a pharmaceutically acceptable carrier; wherein the composition provides a minimum naltrexone blood plasma concentration of about 2.0 ng/mL, following parenteral administration, for a duration of about 8 weeks.

In another embodiment, a pharmaceutical composition comprises Compound 3 or a pharmaceutically acceptable salt thereof, and a pharmaceutically acceptable carrier; wherein the composition provides a minimum naltrexone blood plasma concentration of about 1.0 ng/mL, following parenteral administration, for a duration of about 12 weeks.

In another embodiment, a pharmaceutical composition comprises Compound 3 or a pharmaceutically acceptable salt thereof, and a pharmaceutically acceptable carrier; wherein the composition provides a minimum naltrexone blood plasma concentration of about 1.5 ng/mL, following parenteral administration, for a duration of about 12 weeks.

In another embodiment, a pharmaceutical composition comprises Compound 3 or a pharmaceutically acceptable salt thereof, and a pharmaceutically acceptable carrier; wherein the composition provides a minimum naltrexone blood plasma concentration of about 2.0 ng/mL, following parenteral administration, for a duration of about 12 weeks.

Routes of administration of any of the compositions of the invention include oral, nasal, rectal, intravaginal, parenteral, buccal, inhalation spray, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal, intravesical, intrapulmonary, intraduodenal, intragastrical, intrathecal, subcutaneous, intramuscular, intradermal, intraarterial, intravenous, intrabronchial, inhalation, and topical administration. The term parenteral as used herein includes subcutaneous, intracutaneous, intravenous, intramuscular, intraarticular, intraarterial, intrasynovial, intrasternal, intrathecal, intralesional and intracranial injection or infusion techniques. In one embodiment, the parenteral administration is by injection. In another embodiment, the parenteral administration is by intramuscular injection.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For parenteral administration, the compounds of the invention may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used, such as a polysorbate (e.g., polysorbate 20). Other formulatory agents may include preservatives and buffers as are known in the art, such as a phosphate buffer.

It is contemplated that any one of the compounds of the invention can be present as a co-crystal, solvate, hydrate, polymorph, or the like. Further, the compounds of the invention have a defined stereochemistry and one skilled in the art can also envision other enantiomers, diastereoisomers, or racemates of the compounds of the invention.

The present invention provides methods for the synthesis of the compounds of each of the formulae described herein.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. The following descriptions of synthetic methods are designed to illustrate, but not to limit, general procedures for the preparation of compounds of the present invention.

General methods for the preparation of compounds as described herein are modified by the use of appropriate reagents and conditions, for the introduction of the various moieties found in the Formulae as provided herein. Compounds described herein are synthesized using any suitable procedures starting from compounds that are available from commercial sources, or are prepared using procedures described herein.

The processes generally provide the desired final compound at or near the end of the overall process, although it may be desirable in certain instances to further convert the compound to a pharmaceutically acceptable salt, polymorph, hydrate, solvate or co-crystal thereof.

In the synthetic scheme and examples provided herein, the following abbreviations may be used:

DMF=dimethylformamide

DMAP=4-(dimethylamino)pyridine

DIPEA (DIEA)=N,N-diisopropylethylamine

Pd(dba)$_2$=bis(dibenzylideneacetone)palladium(0)

Pd$_2$(dba)$_3$=tris(dibenzylideneacetone)dipalladium(0)

PyBOP=(benzotriazol-1-yloxy)tripyrrolidinophosphonium hexafluorophosphate

TBS=tert-butyldimethylsilyl

THF=tetrahydrofuran

TFA=trifluoroacetic acid

TEA=triethylamine

TMSOK=potassium trimethylsilanolate

TBME (MTBE)=tert-butyl methyl ether

T$_3$P=propylphosphonic anhydride

XPhos=2-dicyclohexylphosphino-2',4',6'-triisopropylbiphenyl

In one embodiment, a general method for synthesizing one or more compounds of Formula I is provided below (Scheme 1).

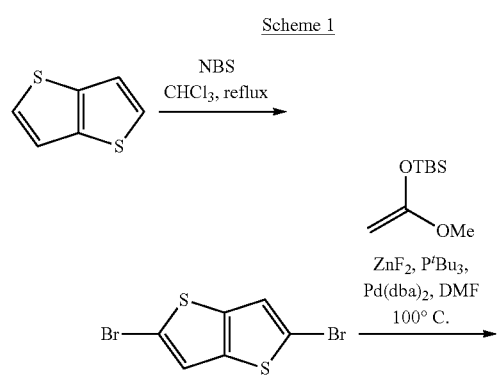

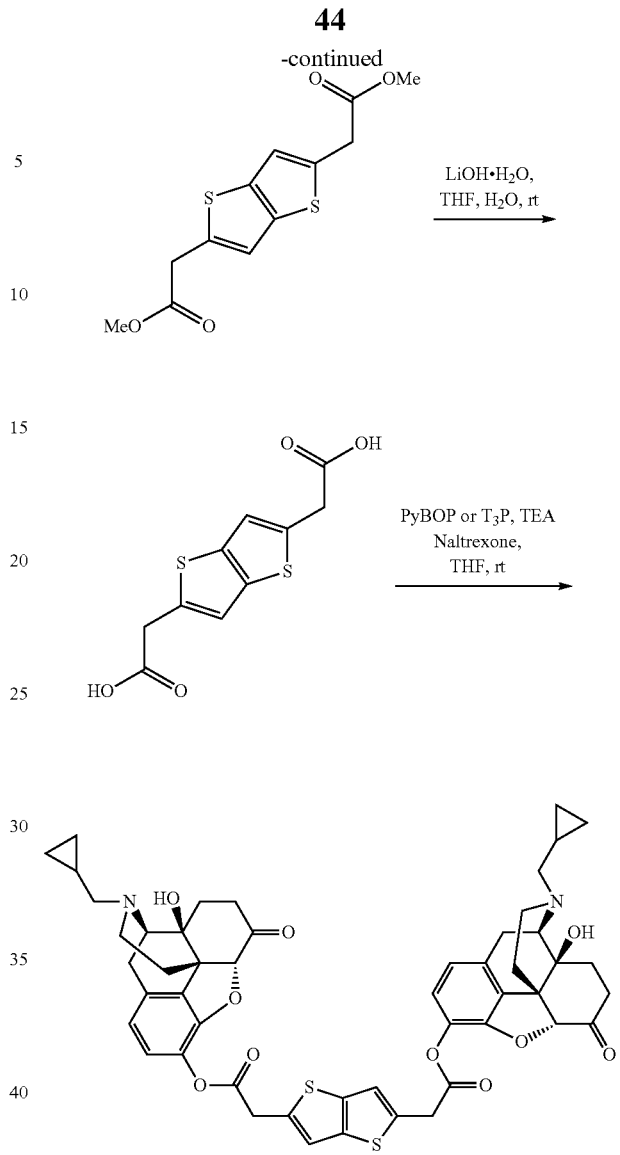

As depicted for Compound 3 in Scheme 1 above, the synthesis of one or more compounds of Formula I can be carried out, for example, by using 2,5-dibromothieno[3,2-b]thiophene as a common precursor, which is commercially available or can be readily synthesized from thieno[3,2-b]thiophene (or the corresponding regioisomer). Pd-mediated cross-coupling using tert-butyl((1-methoxyvinyl)oxy)dimethylsilan, followed by ester hydrolysis, yields 2,2'-(thieno[3,2-b]thiophene-2,5-diyl)diacetic acid. The latter can be coupled to 2 equivalents of naltrexone using standard coupling reagents such as (benzotriazol-1-yloxy)tripyrrolidinophosphonium hexafluorophosphate (PyBOP), propylphosphonic anhydride (T$_3$P), or the like. The route can vary depending on the availability of the starting material or the regiochemistry of the final target.

EXAMPLES

The invention is further illustrated by the following examples, which should not be construed as further limiting.

Examples

Example 1: Synthesis of Compounds of the Invention

1.1 Compound 1

Synthesis of dimethyl 2,2'-(thieno[2,3-b]thiophene-2,5-diyl)diacetate

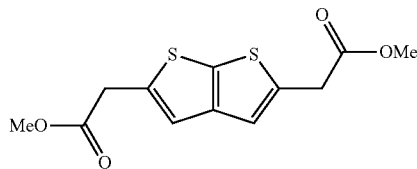 [SMILES: COC(=O)Cc1cc2cc(CC(=O)OC)sc2s1]

A mixture of 2,5-dibromothieno[2,3-b]thiophene (700 mg, 2.35 mmol), bis(dibenzylideneacetone)palladium(0) (270 mg, 0.47 mmol), zinc fluoride (730 mg, 7.05 mmol), 1-(tert-butyldimethylsilyloxy)-1-methoxyethene (2.05 mL, 9.40 mmol) and tri-tert-butylphosphine (1 M in toluene, 0.47 mL, 0.47 mmol) in anhydrous degassed dimethylformamide (14 mL) was irradiated in the microwave at 95° C. for 1 hour 20 minutes. The reaction mixture was quenched with water and extracted with ethyl acetate. The organic layer was washed with brine, dried over sodium sulfate, filtered and concentrated under reduced pressure. The residue was then purified by reverse phase chromatography (C18). The desired fractions were partitioned between ethyl acetate and brine. The layers were separated and the organic layer was dried over sodium sulfate, filtered and concentrated under reduced pressure to give dimethyl 2,2'-(thieno[2,3-b]thiophene-2,5-diyl)diacetate (40 mg, 6% yield).

$^1$H NMR (300 MHz, CDCl$_3$) δ 7.01 (s, 2H), 3.86 (s, 4H), 3.74 (s, 6H).

Synthesis of 2,2'-(thieno[2,3-b]thiophene-2,5-diyl) diacetic Acid

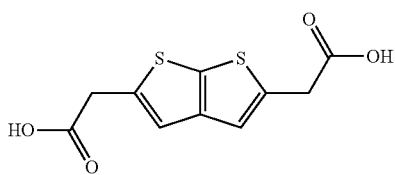 [SMILES: O=C(O)Cc1cc2cc(CC(=O)O)sc2s1]

To a suspension of dimethyl 2,2'-(thieno[2,3-b]thiophene-2,5-diyl)diacetate (85 mg, 0.30 mmol) in tetrahydrofuran (3 mL), methanol (1.5 mL) and water (1.5 mL) was added lithium hydroxide monohydrate (104 mg, 2.39 mmol). The reaction mixture was stirred at room temperature for 1 hour. Tetrahydrofuran and methanol were removed under reduced pressure and the mixture was then diluted with water and acidified with 2 M aqueous solution of hydrochloric acid. The resulting solution was extracted with ethyl acetate (2×), the organic layers were combined, dried over sodium sulfate, filtered and concentrated under reduced pressure to give 2,2'-(thieno[2,3-b]thiophene-2,5-diyl)diacetic acid (90 mg, assumed quantitative yield).

Synthesis of bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-(thieno[2,3-b]thiophene-2,5-diyl)diacetate

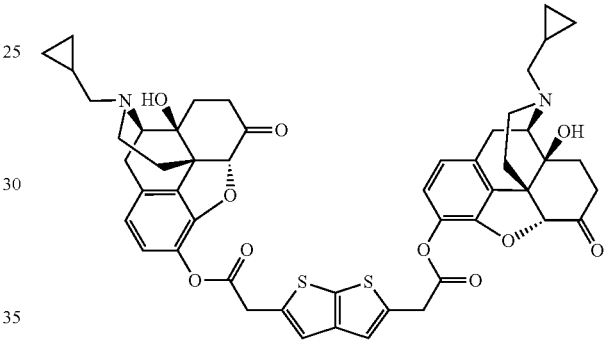

To a suspension of 2,2'-(thieno[2,3-b]thiophene-2,5-diyl) diacetic acid (90 mg, 0.35 mmol) in anhydrous tetrahydrofuran (9 mL), was added triethylamine (0.2 mL, 1.41 mmol), naltrexone (264 mg, 0.77 mmol) and (benzotriazol-1-yloxy) tripyrrolidinophosphonium hexafluorophosphate (438 mg, 0.84 mmol). The reaction mixture was stirred at room temperature for 2 hours. The reaction mixture was then diluted with ethyl acetate and washed with saturated aqueous solution of sodium hydrogen carbonate and brine. The organic layer was dried over sodium sulfate, filtered and concentrated under reduced pressure. The residue was then purified by reverse phase chromatography (C18). The desired fractions were partitioned between ethyl acetate and brine. The layers were separated and the organic layer was dried over sodium sulfate, filtered and concentrated under reduced pressure. The resulting solid was triturated with diethyl ether to give bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-(thieno[2,3-b]thiophene-2,5-diyl)diacetate as a pale yellow solid (136 mg, 43% yield).

$^1$H NMR (300 MHz, CDCl$_3$) δ 7.17 (s, 2H), 6.83 (s, 2H), 6.65 (d, 2H), 4.70 (s, 2H), 4.15 (s, 4H), 3.20 (d, 2H), 3.11-2.97 (m, 4H), 2.73-2.56 (m, 4H), 2.47-2.30 (m, 8H), 2.09-2.17 (m, 2H), 1.92-1.87 (m, 2H), 1.68-1.58 (m, 4H), 1.26 (t, 2H), 0.88-0.86 (m, 2H), 0.56 (q, 4H), 0.15 (q, 4H). [M+H]$^+$ 903.19.

1.2 Compound 2

Synthesis of dimethyl 2,2'-(thieno[2,3-b]thiophene-3,4-diyl)diacetate

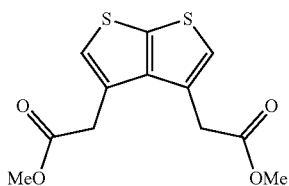 [SMILES: COC(=O)Cc1csc2scc(CC(=O)OC)c12]

To a suspension of bis(dibenzylideneacetone)palladium (0) (81 mg, 0.14 mmol), zinc fluoride (0.83 g, 8.04 mmol) and 3,4-dibromothieno[2,3-b]thiophene (0.80 mg, 2.68 mmol) in N,N-dimethylformamide (12 mL) at room temperature under an atmosphere of nitrogen were added sequentially (1-methoxyvinyl)trimethylsilane (1.75 mL, 8.04 mmol) and tri tri-tert-butyl phosphine (0.27 mL, 1 M sol, in toluene, 0.27 mmol) dropwise. The resulting reaction mixture was heated at 100° C. under an atmosphere of nitrogen for 5 hours then was allowed to cool to room temperature. The mixture was diluted with ethylacetate (20 mL) and was washed with water (2×20 mL). The organic phase was dried over magnesium sulfate, filtered and reduced to dryness under vacuum. The crude material was purified by normal phase chromatography (50% dichloromethane in heptane) to give the desired compound dimethyl 2,2'-(thieno[2,3-b]thiophene-3,4-diyl)diacetate as off-white solid (0.29 g, 30% yield).

$^1$H NMR (400 MHz, CDCl$_3$) δ 7.19 (s, 2H), 3.90 (s, 4H), 3.71 (s, 6H).

Synthesis of 2,2'-(thieno[2,3-b]thiophene-3,4-diyl)diacetic Acid

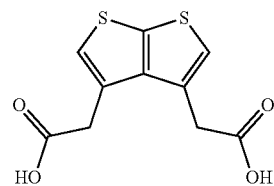 [SMILES: O=C(O)Cc1csc2scc(CC(=O)O)c12]

To a solution of dimethyl 2,2'-(thieno[2,3-b]thiophene-3,4-diyl)diacetate (0.23 g, 0.81 mmol) in tetrahydrofuran (5 mL) was added lithium hydroxide (1.7 mL, 1 M sol. in water, 1.7 mmol) dropwise. The resulting suspension was stirred for 18 hours at room temperature then the reaction was reduced to dryness under vacuum. The crude residue was diluted with water (20 mL), and extracted with tert-butylmethyl ether (3×20 mL). The aqueous phase was acidified to pH 2 using 2 M hydrochloric acid and the resulting precipitate was extracted with ethylacetate (3×20 mL). Combined organic phases were dried over magnesium sulfate, filtered and concentrated in vacuo to afford the desired compound 2,2'-(thieno[2,3-b]thiophene-3,4-diyl)diacetic acid as white solid (0.20 g, 96% yield).

$^1$H NMR (400 MHz, DMSO-d$_6$) δ 12.48 (br. s, 2H), 7.37 (s, 2H), 3.79 (s, 4H).

Synthesis of bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-(thieno[2,3-b]thiophene-3,4-diyl)diacetate

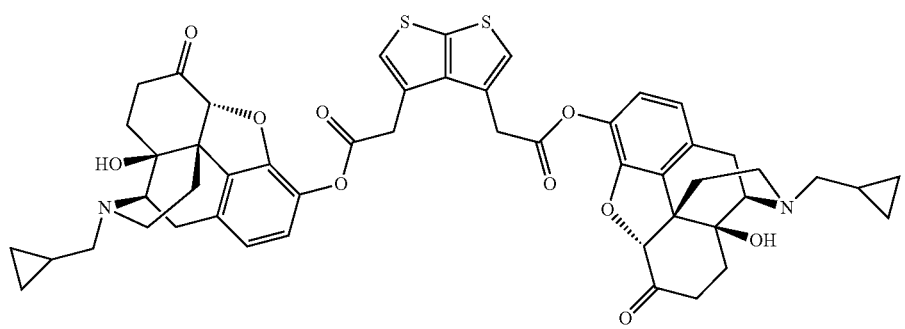 [SMILES: O=C(Cc1csc2scc(CC(=O)Oc3ccc4c5c3O[C@H]3C(=O)CC[C@@]6(O)[C@@H](C4)N(CC4CC4)CC[C@]536)c12)Oc1ccc2c3c1O[C@H]1C(=O)CC[C@@]4(O)[C@@H](C2)N(CC2CC2)CC[C@]314]

To a suspension of 2,2'-(thieno[2,3-b]thiophene-3,4-diyl) diacetic acid (0.20 g, 0.78 mmol), naltrexone (0.53 g, 1.56 mmol) and (benzotriazol-1-yloxy)tripyrrolidinophosphonium hexafluorophosphate (0.83 g, 1.56 mmol) in tetrahydrofuran (10 mL) at room temperature under nitrogen atmosphere was added triethylamine (0.24 mL, 1.72 mmol) dropwise over 3 min. The resulting pale yellow solution was stirred at room temperature for 18 hours. The reaction mixture was diluted with ethylacetate (30 mL), and was washed with a saturated aqueous ammonium chloride solution (3×30 mL). Phases were separated; the aqueous phase was re-extracted with ethyl acetate (50 mL). Combined organic phases were dried over magnesium sulfate, filtered and concentrated in vacuo to a white residue. The crude material was purified by reverse phase chromatography (C18, 5-95% acetonitrile in water with ammonium hydrogen carbonate at pH 9) to give the desired compound bis((4R, 4aS,7aR,12bS)-3-(cyclopropylmethyl)-4a-hydroxy-7-oxo-2,3,4,4a,5,6,7,7a-octahydro-1H-4,12-methanobenzofuro[3, 2-e]isoquinolin-9-yl) 2,2'-(thieno[2,3-b]thiophene-3,4-diyl) diacetate as off-white solid (350 mg. 50% yield).

$^1$H NMR (400 MHz, DMSO-d$_6$) δ 7.59 (s, 2H), 6.86 (d, 2H), 6.72 (d, 2H), 5.14 (br. s, 2H), 4.97 (s, 2H), 4.29 (q, 4H), 3.18 (d, 2H), 3.07 (d, 2H), 2.92 (td, 2H), 2.71-2.52 (m, 6H), 2.44-2.30 (m, 4H), 2.16-2.09 (m, 2H), 1.96 (td, 2H), 1.84-1.76 (m, 2H), 1.51-1.39 (m, 2H), 1.33-1.23 (m, 2H), 0.93-0.83 (m, 2H), 0.55-0.46 (m, 4H), 0.21-0.08 (m, 4H). [M+H]$^+$ 903.30.

1.3 Compound 3

Synthesis of 2,5-dibromothieno[3,2-b]thiophene

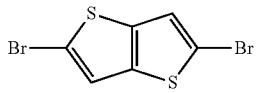

To a solution of thieno[3,2-b]thiophene (10.3 g, 73.5 mmol) in chloroform (200 mL) was added N-bromosuccinimide (32.7 g, 183.8 mmol). The mixture was heated at reflux for 18 hours. The reaction mixture was allowed to cool to room temperature before being diluted with dichloromethane (50 mL) and washed with distilled water (2×100 mL), sodium hydrogen carbonate saturated solution (100 mL), and ammonium chloride saturated solution (100 mL) and brine (100 mL). The organic layer was passed through a phase separator and concentrated in vacuo, yielding 2,5-dibromothieno[3,2-b]thiophene (21.8 g, 99%) as a grey solid.

$^1$H NMR (400 MHz, CDCl$_3$): δ 7.16 (s, 2H).

Synthesis of dimethyl 2,2'-(thieno[3,2-b]thiophene-2,5-diyl)diacetate

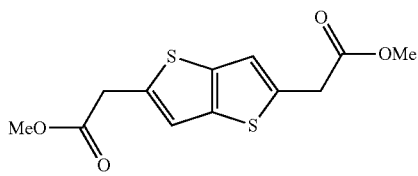 [SMILES: COC(=O)Cc1cc2sc(CC(=O)OC)cc2s1]

A two-necked flask was charged with 2,5-dibromothieno [3,2-b]thiophene (5.0 g, 16.8 mmol), zinc fluoride (5.2 g, 50.0 mmol) and bis(dibenzylideneacetone)palladium(0) (480 mg, 0.84 mmol). N,N-dimethylformamide (50 mL) was added to the flask, followed by tri-tert-butylphosphine (1.67 mL, 1.68 mmol, 1 M in toluene) and tert-butyl((1-methoxyvinyl)oxy)dimethylsilane (9.2 mL, 7.9 g, 42.0 mmol). The reaction mixture was heated at 100° C. for 18 hours. The reaction mixture was allowed to cool to room temperature. Most of the solvent was removed in vacuo and the crude product was re-dissolved in ethyl acetate (50 mL) and filtered through a Celite pad. The concentrated filtrate was applied directly on silica column (heptane/dichloromethane, 6:4). The appropriate fractions were combined and concentrated in vacuo yielding dimethyl 2,2'-(thieno[3, 2-b]thiophene-2,5-diyl)diacetate as a yellow solid (2.0 g isolated). Silica column chromatography on collected mixed fractions (ethyl acetate/n-heptane, 1:4) yielded another batch of dimethyl 2,2'-(thieno[3,2-b]thiophene-2,5-diyl)diacetate (400 mg). In total 2.4 g of dimethyl 2,2'-(thieno[3,2-b] thiophene-2,5-diyl)diacetate were isolated, 52% yield.

$^1$H NMR (400 MHz, CDCl$_3$): δ 7.07 (s, 2H), 3.88 (s, 4H), 3.74 (s, 6H).

Synthesis of 2,2'-(thieno[3,2-b]thiophene-2,5-diyl) diacetic Acid

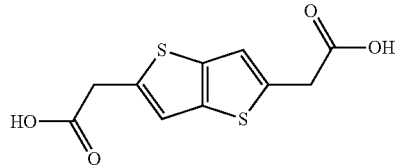 [SMILES: O=C(O)Cc1cc2sc(CC(=O)O)cc2s1]

To a solution of dimethyl 2,2'-(thieno[3,2-b]thiophene-2, 5-diyl)diacetate (2.0 g, 7.0 mmol) in tetrahydrofuran (15 mL) and distilled water (5 mL) was added LiOH.H$_2$O (587 mg, 14.0 mmol). The mixture was stirred at room temperature for 2 hours. The reaction mixture was diluted with ethyl acetate (50 mL) and ammonium chloride (100 mL). pH was then adjusted to pH 2 with 2 M hydrochloric acid. The aqueous layer was further extracted with ethyl acetate (3×50 mL). The combined organic layer was dried with anhydrous sodium sulfate and concentrated in vacuo yielding 2,2'-(thieno[3,2-b]thiophene-2,5-diyl)diacetic acid as a yellow solid (1.78 g, 99%).

$^1$H NMR (400 MHz, DMSO-d$_6$): δ 7.21 (s, 2H), 3.87 (s, 4H).

Synthesis of bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-(thieno[3,2-b]thiophene-2,5-diyl)diacetate

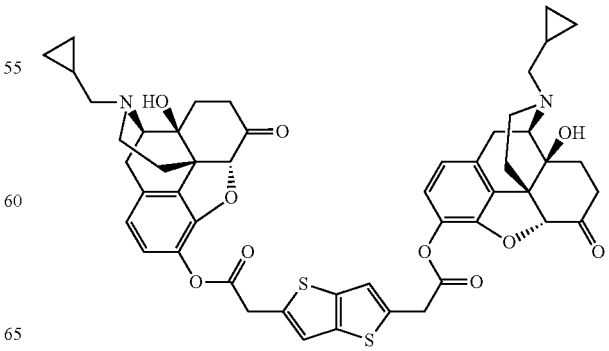

To a suspension of 2,2'-(thieno[3,2-b]thiophene-2,5-diyl) diacetic acid (1.68 g, 6.58 mmol) in tetrahydrofuran (30 mL) was added triethylamine (1.84 mL, 13.13 mmol), (benzotriazol-1-yloxy)tripyrrolidinophosphonium hexafluorophosphate ((benzotriazol-1-yloxy)tripyrrolidinophosphonium hexafluorophosphate) (6.83 g, 13.13 mmol) and naltrexone (4.48 mg, 13.13 mmol). The reaction was stirred at RT for 18 hours under an atmosphere of nitrogen. Analysis of the reaction mixture by LCMS showed ca. 70% consumption of starting material. The reaction mixture was diluted with ethylacetate (100 mL) and sodium hydrogen carbonate saturated solution (100 mL). The organic layer was dried with anhydrous sodium sulfate and concentrated in vacuo. Crude material was purified by reverse phase chromatography (C18, 30-100% acetonitrile in water with ammonium bicarbonate buffer at pH 9). The resulting orange solid was freeze-dried from acetonitrile/distilled water yielding the title compound as a yellow solid (2.52 g, 42%).

$^1$H NMR (400 MHz, DMSO-d$_6$): 7.39 (s, 2H), 6.87 (d, 2H), 6.73 (d, 2H), 5.15 (br s, 2H), 4.95 (s, 2H), 4.32 (s, 4H), 3.17 (d, 2H), 3.08 (d, 2H), 2.92 (dt, 2H), 2.72-2.55 (m, 4H), 2.45-2.29 (m, 6H), 2.11 (d, 2H), 1.95 (td, 2H), 1.80 (d, 2H), 1.46 (td, 2H), 1.33-1.23 (m, 2H), 0.88 (m, 2H), 0.48 (d, 4H), 0.13 (d, 4H). [M+H]$^+$ 903.33.

1.4 Compound 4

Synthesis of dimethyl 2,2'-(3,6-dimethylthieno[3,2-b]thiophene-2,5-diyl)diacetate

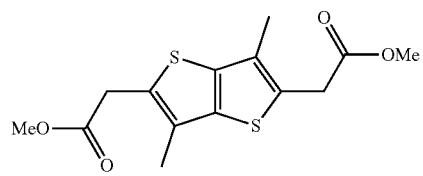 [SMILES: COC(=O)Cc1sc2c(C)c(CC(=O)OC)sc2c1C]

To a solution of 2,5-dibromo-3,6-dimethylthieno[3,2-b]thiophene (815 mg, 2.50 mmol) in dry N,N-dimethylformamide (10 mL) under nitrogen, was added zinc fluoride (775 mg, 7.50 mmol), bis(dibenzylideneacetone)palladium(0) (71 mg, 0.13 mmol), a solution of tri-tert-butylphosphine in toluene (1 M, 0.25 mL, 0.25 mmol), tert-butyl((1-methoxyvinyl)oxy)dimethylsilane (1.4 mL, 6.25 mmol). The reaction was heated to 100° C. for 18 hours and then allowed to cool to room temperature. The reaction was quenched by addition of water (10 mL) and was extracted with ethyl acetate (3×10 mL). The combined organic phases were dried over magnesium sulfate, filtered and concentrated to dryness to give a black oil. This was purified by silica chromatography, eluted with a gradient of 5-20% ethyl acetate in heptane to give dimethyl 2,2'-(3,6-dimethylthieno[3,2-b]thiophene-2,5-diyl)diacetate as a yellow solid (375 mg, 48% yield).

$^1$H NMR (400 MHz, CDCl$_3$) δ 3.78 (s, 4H), 3.70 (s, 6H), 2.24 (s, 6H).

Synthesis of Give 2,2'-(3,6-dimethylthieno[3,2-b]thiophene-2,5-diyl)diacetic Acid

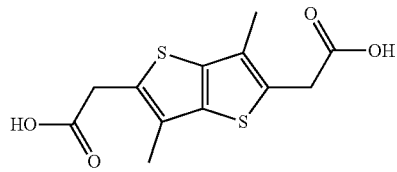 [SMILES: Cc1c(CC(=O)O)sc2c(C)c(CC(=O)O)sc12]

To a solution of dimethyl 2,2'-(3,6-dimethylthieno[3,2-b]thiophene-2,5-diyl)diacetate (361 mg, 1.15 mmol) in a mixture of tetrahydrofuran:water (1:1, 20 mL) was added lithium hydroxide monohydrate (107 mg, 2.54 mmol). The reaction was stirred for 30 minutes at room temperature, diluted with water (20 mL) and extracted with methyl tert-butyl ether (2×10 mL). The aqueous phase was acidified to pH 1 with hydrochloric acid 2 N (1 mL) and extracted with ethyl acetate (3×15 mL). The combined organic phases were washed with saturated ammonium chloride aqueous solution (10 mL), brine (10 mL), dried over magnesium sulfate, filtered and concentrated to dryness to give 2,2'-(3,6-dimethylthieno[3,2-b]thiophene-2,5-diyl)diacetic acid as a yellow solid (320 mg, 98%).

$^1$H NMR (400 MHz, DMSO-d$_6$) δ 3.76 (s, 4H), 2.14 (s, 6H).

Synthesis of bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-(3,6-dimethylthieno[3,2-b]thiophene-2,5-diyl)diacetate

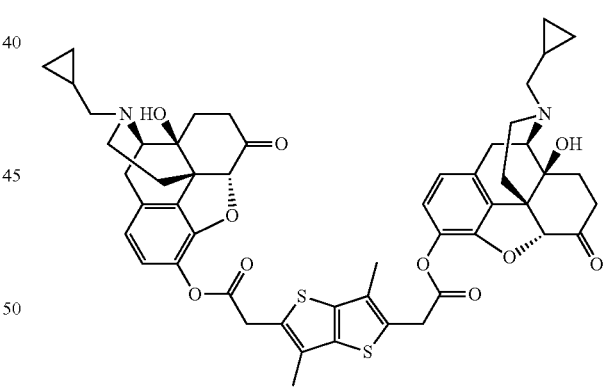

To a solution of 2,2'-(3,6-dimethylthieno[3,2-b]thiophene-2,5-diyl)diacetic acid (320 mg, 1.13 mmol) in dry tetrahydrofuran (12 mL) under nitrogen, was added naltrexone (768 mg, 2.25 mmol), triethylamine (0.31 mL, 2.25 mmol) and (benzotriazol-1-yloxy)tripyrrolidinophosphonium hexafluorophosphate (1.12 g, 2.25 mmol). The reaction was stirred overnight at room temperature then was concentrated to dryness, leading to a red oil. This was purified by reverse phase chromatography, eluted with a gradient of 0-100% acetonitrile in pH 9 ammonium bicarbonate buffer to give bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-(3, 6-dimethylthieno[3,2-b]thiophene-2,5-diyl)diacetate as a yellow solid (593 mg, 56% yield).

$^1$H NMR (400 MHz, DMSO-d$_6$) δ 6.81 (d, 2H), 6.68 (d, 2H), 5.10 (s, 2H), 4.90 (s, 2H), 4.20 (s, 4H), 3.13 (d, 2H), 3.03 (d, 2H), 2.87 (td, 2H), 2.52-2.63 (m, 4H), 2.28-2.38 (m, 4H), 2.24 (s, 6H), 2.07 (dt, 2H), 1.91 (dt, 2H), 1.75 (dt, 2H), 1.40 (td, 2H), 1.25 (dd, 2H), 0.81-0.86 (m, 2H), 0.42-0.47 (m, 4H), 0.07-0.01 (m, 4H). [M+2H]$^{2+}$ 466.10.

1.5 Compound 5

Synthesis of dibutyl 3,3'-(thieno[3,2-b]thiophene-2,5-diyl)(2E,2'E)-diacrylate

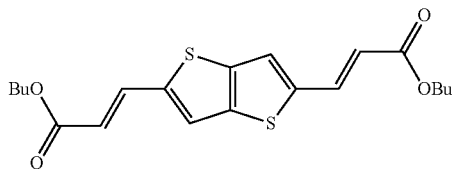

Into a 100 mL round-bottomed flask were added thieno[3,2-b]thiophene (700 mg, 4.99 mol), oxo(2,2,2-trifluoroacetyl)silver (4.4 g, 19.97 mol), (acetyloxy)palladio acetate (560.4 mg, 2.50 mol) and butyl prop-2-enoate (2.56 g, 19.97 mol) in propionic acid (25 mL) at room temperature. The resulting mixture was stirred for 48 h at 50° C. under nitrogen atmosphere. The reaction was monitored by LCMS and TLC. The resulting mixture was diluted with CH$_2$Cl$_2$ (200 mL) and washed with water (3×100 mL). The organic layers were dried over anhydrous Na$_2$SO$_4$. After filtration, the filtrate was concentrated under reduced pressure. The residue was purified by prep-TLC (CH$_2$Cl$_2$/PE=5:1) to afford 3,3'-(thieno[3,2-b]thiophene-2,5-diyl)(2E,2'E)-diacrylate (1.4 g, 60.7%) as a yellow solid.

$^1$H NMR (400 MHz, CDCl$_3$) δ 7.81 (d, 1H), 7.38 (s, 1H), 6.29 (d, 1H), 4.23 (t, 2H), 1.72 (q, 2H), 1.46 (q, 2H), 0.99 (t, 3H). [M+H]$^+$=393.25.

Synthesis of dibutyl 3,3'-(thieno[3,2-b]thiophene-2,5-diyl)dipropionate

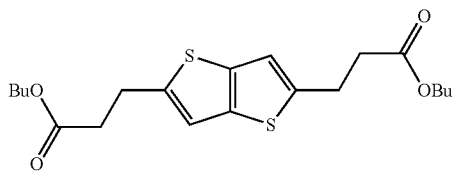

Into a 100 mL round-bottom flask were added butyl 3,3'-(thieno[3,2-b]thiophene-2,5-diyl)(2E,2'E)-diacrylate (500 mg, 1.27 mmol) and cobalt chloride hexahydrate (151.5 mg, 0.64 mmol) at room temperature. To the above mixture was added NaBH$_4$ (385.5 mg, 10.19 mmol) in portions at room temperature. The resulting mixture was stirred for additional 24 h at room temperature. The reaction was monitored by LCMS. The reaction was quenched with water/ice at room temperature. The resulting mixture was extracted with EtOAc (3×150 mL). The combined organic layers were washed with brine (2×50 mL), dried over anhydrous Na$_2$SO$_4$. After filtration, the filtrate was concentrated under reduced pressure. This resulted in dibutyl 3,3'-(thieno[3,2-b]thiophene-2,5-diyl)dipropionate (400 mg, 63.4%) as a light yellow oil. The crude product was used in the next step directly without further purification.

$^1$H NMR (400 MHz, CDCl$_3$) δ 6.93 (s, 1H), 4.11 (d, 2H), 3.21 (t, 2H), 2.72 (t, 2H), 1.61 (d, 2H), 1.39 (d, 2H), 0.92 (d, 3H). [M+H]$^+$=397.15.

Synthesis of 3,3'-(thieno[3,2-b]thiophene-2,5-diyl)dipropionic Acid

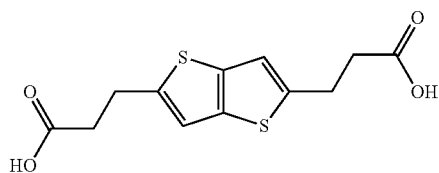 [SMILES: O=C(O)CCc1cc2sc(CCC(=O)O)cc2s1]

Into a 50 mL round-bottom flask were added butyl dibutyl 3,3'-(thieno[3,2-b]thiophene-2,5-diyl)dipropionate (400 mg, 1.01 mmol) and NaOH (2.0 mL, 50.44 mmol) in 30 mL MeOH/THF (2:1) at room temperature. The resulting mixture was stirred for 4 h at room temperature under nitrogen atmosphere. The reaction was quenched with water/ice at room temperature. The mixture was acidified to pH 2 with conc. HCl. The resulting mixture was extracted with EtOAc (3×50 mL). The combined organic layers were washed with brine (2×10 mL), dried over anhydrous Na$_2$SO$_4$. After filtration, the filtrate was concentrated under reduced pressure. The crude product was used in the next step directly without further purification.

$^1$H NMR (400 MHz, DMSO-d$_6$) δ 12.13 (s, 1H), 7.11 (s, 1H), 3.07 (t, 2H), 2.61 (t, 2H). [M+H]$^+$=285.05.

Synthesis of bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 3,3'-(thieno[3,2-b]thiophene-2,5-diyl)dipropionate

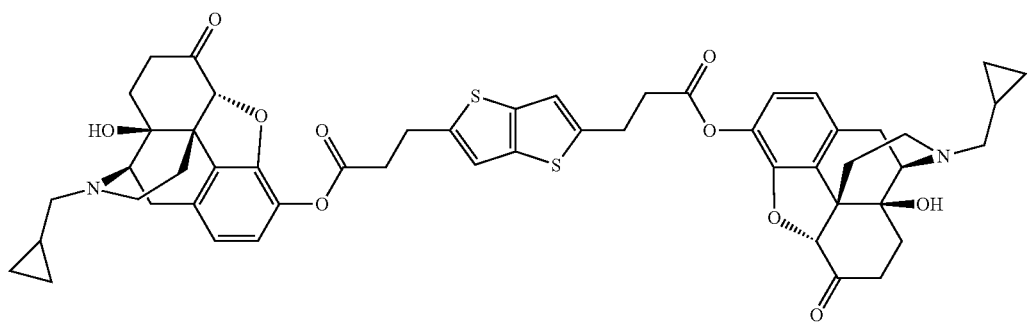 [SMILES: O=C(CCc1cc2sc(CCC(=O)Oc3ccc4c5c3O[C@H]3C(=O)CC[C@@]6(O)[C@@H](C4)N(CC4CC4)CC[C@]536)cc2s1)Oc1ccc2c3c1O[C@H]1C(=O)CC[C@@]4(O)[C@@H](C2)N(CC2CC2)CC[C@]314]

Into a 8 mL sealed tube were added 3,3'-(thieno[3,2-b]thiophene-2,5-diyl)dipropionic acid (400 mg, 1.41 mmol), naltrexone (1.06 g, 3.09 mmol), PyBOP (1.1 g, 2.11 mmol), DMAP (34.4 mg, 0.28 mmol) and DIPEA (545.4 mg, 4.22 mmol) in DMF (25 mL) at room temperature. The resulting mixture was stirred for overnight at room temperature under nitrogen atmosphere. The reaction was quenched by the addition of water (10 mL) at room temperature. The resulting mixture was extracted with EtOAc (3×50 mL). The combined organic layers were washed with brine (2×10 mL), dried over anhydrous Na$_2$SO$_4$. After filtration, the filtrate was concentrated under reduced pressure. The residue was purified by reverse flash chromatography (C18 using MeCN in water, 10-100% gradient). The crude product (800 mg) was purified by prep-HPLC (C18, water/acetonitrile) to afford bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 3,3'-(thieno[3,2-b]thiophene-2,5-diyl)dipropionate (139 mg, 16.5%) as a white solid.

$^1$H NMR (400 MHz, DMSO-d$_6$) δ 7.26 (s, 2H), 6.82 (d, 2H), 6.72 (d, 2H), 5.16 (s, 2H), 4.93 (s, 2H), 3.27-3.14 (m, 6H), 3.08 (d, 2H), 2.99 (t, 4H), 2.92 (dd, 2H), 2.72-2.54 (m, 4H), 2.39 (t, 6H), 2.16-2.09 (m, 2H), 2.00-1.91 (m, 2H), 1.80 (d, 2H), 1.47 (t, 2H), 1.30 (d, 2H), 0.96-0.83 (m, 2H), 0.56-0.44 (m, 4H), 0.20-0.10 (m, 4H). [M+H]$^+$=931.15.

1.6 Compound 6

Synthesis of thieno[3,2-b]thiophene-3,6-dicarbaldehyde

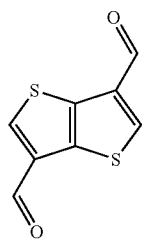

To a cooled (dry ice—acetone bath) solution of n-butyllithium (1.6 M in hexane, 4.7 mL, 7.5 mmol) in tetrahydrofuran (10 mL) was added dropwise a solution of 3,6-dibromothieno[3,2-b]thiophene (1.0 g, 3.35 mmol) in tetrahydrofuran (8 mL) over 35 minutes under an atmosphere of argon. The mixture was stirred on the cooling bath for 2 hours. To this was added N,N-dimethylformamide (1.3 mL) in one portion and stirring maintained on the cooling bath for 10 minutes before allowing to room temperature for 1.5 hours. The suspension was quenched with saturated aqueous solution of sodium bicarbonate and extracted with ethyl acetate (2×) then dichloromethane [note—the aqueous layer contained lots of solid]. The aqueous layer was filtered, washed with water and dried under vacuum to give 290 mg of thieno[3,2-b]thiophene-3,6-dicarbaldehyde. The combined organic extracts were dried over sodium sulfate, filtered and concentrated under reduced pressure. The residue was triturated in a minimum amount of ethyl acetate, filtered and washed with ethyl acetate and dried under vacuum to give thieno[3,2-b]thiophene-3,6-dicarbaldehyde (253 mg, combined 83% yield).

$^1$H NMR (300 MHz, CDCl$_3$) δ 10.03 (s, 2H), 8.37 (s, 2H).

Synthesis of 3,6-bis((1,3-dithian-2-ylidene)methyl)thieno[3,2-b]thiophene

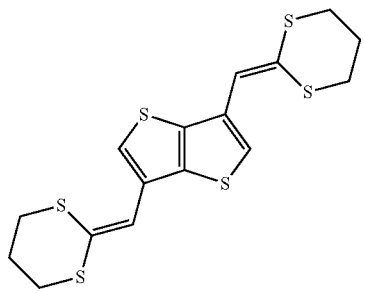 [SMILES: C(=C1SCCCS1)c1csc2c(C=C3SCCCS3)csc12]

To a cooled (dry ice—acetone bath) solution of 2-trimethylsilyl-1,3-dithiane (1.0 mL, 5.2 mmol) in tetrahydrofuran (10 mL) was added dropwise n-butyllithium (1.6 M in hexane, 3.2 mL, 5.2 mmol) under an atmosphere of argon. This was allowed to 0° C. for 10 minutes before cooling again (dry ice—acetone). To this was added thieno[3,2-b]thiophene-3,6-dicarbaldehyde (250 mg, 1.3 mmol) in one portion. The suspension was stirred rapidly on the cooling bath for 2 hours before allowing warming slowly to room temperature over 2.5 hours, after which time a solution was obtained. The reaction was quenched with water and extracted with ethyl acetate (2×) [note—the organic layer contained lots of solid]. The organic layer was filtered, washed with ethyl acetate and dried under vacuum to give 168 mg of 3,6-bis((1,3-dithian-2-ylidene)methyl)thieno[3,2-b]thiophene. The combined organic extracts were dried over sodium sulfate, filtered and concentrated under reduced pressure. The residue was triturated in a minimum amount of dichloromethane, filtered and washed with dichloromethane and dried under vacuum to give 3,6-bis((1,3-dithian-2-ylidene)methyl)thieno[3,2-b]thiophene (38 mg, combined 206 mg, 41% yield).

$^1$H NMR (300 MHz, CDCl$_3$) δ 7.64 (s, 2H), 6.77 (s, 2H), 3.02 (t, 8H), 2.23 (dt, 4H).

Synthesis of 2,2'-(thieno[3,2-b]thiophene-3,6-diyl)diacetic Acid

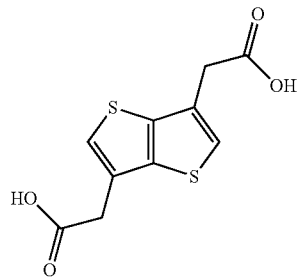 [SMILES: O=C(O)Cc1csc2c(CC(=O)O)csc12]

A suspension of 3,6-bis((1,3-dithian-2-ylidene)methyl)thieno[3,2-b]thiophene (168 mg, 0.42 mmol) in acetic acid (8 mL) and concentrated hydrochloric acid (3.2 mL) was heated at reflux (with a bleach scrubber attached to the condenser) for 3 hours (note: suspension clears after 30 minutes but a dark oily substance persists). The volatiles were removed under vacuum then the residue was azeotroped with toluene (4×) and dried under vacuum to give 2,2'-(thieno[3,2-b]thiophene-3,6-diyl)diacetic acid (114 mg, assumed quantitative yield).

$^1$H NMR (300 MHz, DMSO-d$_6$) δ 7.42 (s, 2H), 3.67 (s, 4H). [M+H]$^+$ 257.00.

Synthesis of bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-(thieno[3,2-b]thiophene-3,6-diyl)diacetate

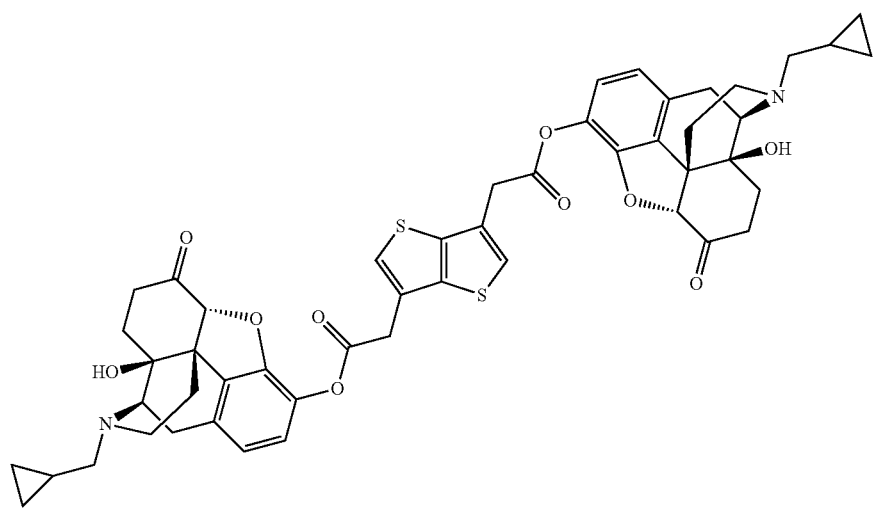 [SMILES: O=C(Cc1csc2c(CC(=O)Oc3ccc4c5c3O[C@H]3C(=O)CC[C@@]6(O)[C@@H](C4)N(CC4CC4)CC[C@]536)csc12)Oc1ccc2c3c1O[C@H]1C(=O)CC[C@@]4(O)[C@@H](C2)N(CC2CC2)CC[C@]314]

Naltrexone (296 mg, 0.87 mmol) and (benzotriazol-1-yloxy)tripyrrolidinophosphonium hexafluorophosphate (491 mg, 0.95 mmol) were added to a solution of 2,2'-(thieno[3,2-b]thiophene-3,6-diyl)diacetic acid (101 mg, 0.39 mmol) in tetrahydrofuran (14 mL) and triethylamine (0.22 mL, 1.56 mmol) and the suspension was stirred at room temperature for 2 hours. The reaction was quenched with saturated aqueous solution of sodium bicarbonate, extracted with dichloromethane (3x), dried over sodium sulfate, filtered and concentrated under reduced pressure. The residue was purified by silica chromatography, eluted with 33% heptanes in dichloromethane containing 5% triethylamine. The residue was then triturated with diethyl ether to give bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-(thieno[3,2-b]thiophene-3,6-diyl)diacetate (182 mg, 52% yield).

$^1$H NMR (300 MHz, CDCl$_3$) δ 7.43 (s, 2H), 6.83 (d, 2H), 6.65 (d, 2H), 5.20 (br s, 2H), 4.70 (d, 2H), 4.02 (s, 4H), 3.19 (d, 2H), 3.11-2.97 (m, 4H), 2.69 (dd, 2H), 2.62 (dd, 2H), 2.47-2.30 (m, 8H), 2.13 (dt, 2H), 1.91-1.85 (m, 2H), 1.60 (dt, 4H), 0.91-0.80 (m, 2H), 0.59-0.53 (m, 4H), 0.17-0.12 (m, 4H). [M+2H]$^{2+}$ 452.00.

1.7 Compound 2i

Synthesis of 2-(4-(2-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-2-oxoethyl)thieno[2,3-b]thiophen-3-yl)acetic Acid

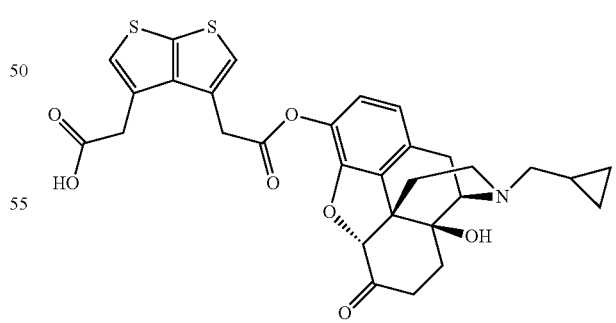

To a solution of 2,2'-(thieno[2,3-b]thiophene-3,4-diyl)diacetic acid (150 mg, 0.59 mmol) in tetrahydrofuran (7.5 mL) was added naltrexone (200 mg, 0.59 mmol) and triethylamine (0.09 mL, 0.63 mmol). To this solution was added (benzotriazol-1-yloxy)tripyrrolidinophosphonium hexafluorophosphate (312 mg, 0.59 mmol) and the reaction was stirred at room temperature for 18 hours. The reaction mixture was reduced to dryness and the residue was purified by reverse phase chromatography (C18). The relevant fractions were collected and dried in a freeze-drier to give 2-(4-(2-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-2-oxoethyl)thieno[2,3-b]thiophen-3-yl)acetic acid as a white solid (110 mg, 31%).

$^1$H NMR (400 MHz, DMSO-d$_6$) δ 7.57 (s, 1H), 7.40 (s, 1H), 6.87 (d, 1H), 6.74 (d, 1H), 4.94 (s, 1H), 4.22 (d, 1H), 3.85 (d, 1H), 3.18 (d, 1H), 3.07 (d, 1H), 2.91 (td, 1H), 2.73-2.56 (m, 3H), 2.44-2.30 (m, 4H), 2.13-2.04 (m, 1H), 1.99-1.92 (m, 1H), 1.82-1.75 (m, 1H), 1.46 (td, 1H), 1.32-1.23 (m, 1H), 0.92-0.83 (m, 1H), 0.55-0.44 (m, 2H), 0.14-0.08 (m, 2H).

1.8 Compound 3i

Synthesis of 2-(5-(2-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-2-oxoethyl)thieno[3,2-b]thiophen-2-yl)acetic Acid

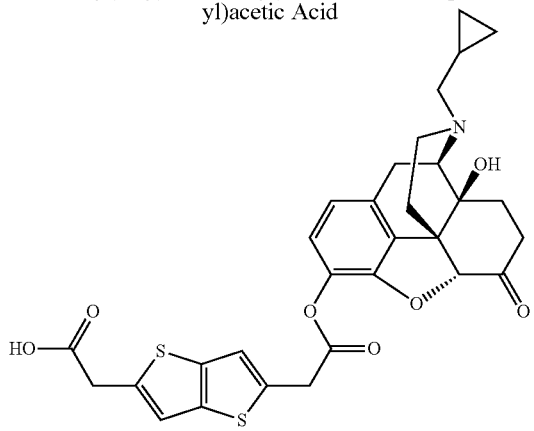

To a solution of 2,2'-(thieno[3,2-b]thiophene-2,5-diyl) diacetic acid (4.0 g, 15.61 mmol) in tetrahydrofuran (200 mL) was added naltrexone (5.33 g, 15.61 mmol) and triethylamine (2.18 mL, 1.58 g, 15.61 mmol). To the dark brown solution was added (benzotriazol-1-yloxy)tripyrrolidinophosphonium hexafluorophosphate (8.14 g, 15.61 mmol) portion-wise over 10 minutes and the reaction left to stir at room temperature for 18 hours. The reaction was reduced to dryness to give a dark brown solid. The crude material was purified by reverse phase chromatography (5.0 g batches, water with 0.1% ammonium formate and acetonitrile using 5-50% gradient). The correct fractions were collected and dried in the freeze drier to give 2-(5-(2-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-2-oxoethyl)thieno[3,2-b]thiophen-2-yl) acetic acid as a pale yellow solid (2.8 g). The solid was further purified by reverse phase chromatography. The correct fractions were collected and reduced to dryness using freeze drier to give 2-(5-(2-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-2-oxoethyl)thieno[3,2-b]thiophen-2-yl)acetic acid (2.2 g, 24%).

$^1$H NMR (396 MHz, DMSO-d$_6$) δ 7.32 (s, 1H), 7.19 (s, 1H), 6.83 (d, 1H), 6.69 (d, 1H), 4.91 (s, 1H), 4.26 (s, 2H), 3.83 (d, 2H), 3.14 (d, 1H), 3.04 (d, 1H), 2.88 (td, 1H), 2.70-2.57 (m, 2H), 2.41-2.26 (m, 3H), 2.07 (dt, 1H), 1.92 (td, 1H), 1.82-1.65 (m, 1H), 1.42 (td, 1H), 1.33-1.19 (m, 1H), 0.84 (tq, 1H), 0.58-0.33 (m, 2H), 0.19-0.03 (m, 2H). [M+H]$^+$ 580.20.

1.9 Compound 5i

Synthesis of 3-(5-(3-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-3-oxopropyl)thieno[3,2-b]thiophen-2-yl)propanoic Acid

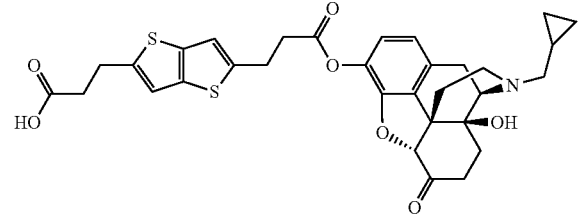 [SMILES: O=C(O)CCc1cc2sc(CCC(=O)Oc3ccc4c5c3O[C@H]3C(=O)CC[C@@]6(O)[C@@H](C4)N(CC4CC4)CC[C@]536)cc2s1]

Into a 50 mL round-bottomed flask were added naltrexone (80 mg, 0.23 mmol), 3,3'-(thieno[3,2-b]thiophene-2,5-diyl) dipropionic acid (333.1 mg, 1.17 mmol), EDCI (44 mg, 0.23 mmol) and DMAP (2.9 mg, 0.02 mmol) in DCM (20 mL) at room temperature. The resulting mixture was stirred for overnight at room temperature under nitrogen atmosphere. The crude product (100 mg) was purified by prep-HPLC with the following conditions (water containing 0.1% formic acid with acetonitrile; 20-55% gradient) to afford 3-(5-(3-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-3-oxopropyl)thieno[3,2-b]thiophen-2-yl)propanoic acid (34.5 mg, 24.2%) as a white solid.

$^1$H NMR (400 MHz, DMSO-d$_6$) δ 7.24 (s, 1H), 7.13 (s, 1H), 6.82 (d, 1H), 6.73 (d, 1H), 4.93 (d, 1H), 3.26-3.15 (m, 2H), 3.08 (m, 3H), 2.95 (m, 3H), 2.72-2.58 (m, 3H), 2.40 (m, 3H), 2.13 (d, 1H), 1.96 (t, 1H), 1.81 (d, 1H), 1.53-1.41 (m, 1H), 1.30 (d, 1H), 0.89 (s, 1H), 0.50 (d, 2H), 0.15 (d, 2H). [M+H]$^+$=608.10.

1.10 Compound 6i

Synthesis of 2-(6-(2-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-2-oxoethyl)thieno[3,2-b]thiophen-3-yl)acetic Acid

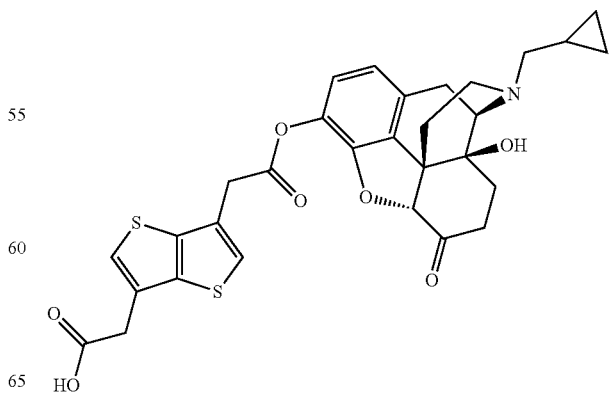

To a solution of 2,2'-(thieno[3,2-b]thiophene-3,6-diyl) diacetic acid (50 mg, 0.19 mmol) in tetrahydrofuran (2.5 mL) was added naltrexone (64 mg, 0.19 mmol), triethylamine (0.02 mL, 0.19 mmol) and (benzotriazol-1-yloxy)tripyrrolidinophosphonium hexafluorophosphate (100 mg, 0.19 mmol). The reaction mixture was stirred at room temperature for 16 hours and then concentrated under reduced pressure. The crude material was purified by reverse phase chromatography (C18) and freeze dried to give 2-(6-(2-(((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)-2-oxoethyl)thieno[3,2-b]thiophen-3-yl)acetic acid (26 mg, 23%).

$^1$H NMR (400 MHz, CDCl$_3$) δ 7.39 (s, 1H), 7.21 (s, 1H), 6.77 (d, 1H), 6.58 (d, 1H), 4.64 (s, 1H), 3.98 (s, 2H), 3.73 (s, 2H), 3.29-3.31 (m, 1H), 2.97-3.01 (m, 1H), 2.80-2.96 (m, 1H), 2.60-2.61 (m, 2H), 2.42-2.44 (m, 2H), 2.10-2.23 (m, 2H), 1.86-1.89 (m, 1H), 1.49-1.55 (m, 2H), 0.90-0.91 (m, 1H), 0.52-0.54 (m, 2H), 0.14-0.15 (m, 2H). [M+H]$^+$ 580.00.

Example 2: Whole Blood Stability Assay

Naltrexone prodrug stability was assessed using freshly collected whole blood (within 24-hr collection) from pooled human (n=3) donors. The incubation mixtures were prepared by spiking the prodrugs into pre-warmed (37 degrees C.) fresh whole blood to a final concentration of 50 nM. After gentle mixing, aliquots of incubation mixtures were immediately transferred into four different 96-deep well plates. One plate was used for each time point. The plates were incubated at 37 degrees C. at a shaking speed of 100 rpm. At time points 15, 30, 60 and 120 minutes, the reaction was quenched by addition of a mixture of water and acetonitrile containing the internal standard (naltrexone-D$_3$). Time point 0 minutes was prepared separately by spiking the prodrugs into a quenched whole blood to obtain a final concentration of 50 nM. All samples were vortexed at a low speed for 15 min and centrifuged at 3900 rpm for 15 min. Supernatants were transferred into 96-well plates for LC-MS/MS analysis to monitor the depletion of the prodrugs and the formation of naltrexone.

The amount of remaining prodrug and released naltrexone for each sample was quantitated against the calibration curves prepared with the whole blood. The human whole blood was purchased from BioreclamationIVT (Westbury, N.Y., USA). Naltrexone-D$_3$ was purchased from Cerilliant® (Round Rock, Tex., USA). Table C shows the half-life of the prodrugs and the amount of naltrexone (in equivalents) measured in whole blood at the 2 hour timepoint. Where multiple runs have been completed, average values are reported.

TABLE C

| Prodrug | t$_{1/2}$ at 37 degrees C. in human whole blood (min) | Naltrexone formed in human whole blood at 2 hours (equiv.) |
|---|---|---|
| Compound 1 | 11.0 | 1.70 |
| Compound 2 | 15.7 | 1.64 |
| Compound 3 | 6.46 | 1.48 |
| Compound 4 | 20.7 | 1.29 |
| Compound 5 | 17.1 | 1.43 |
| Compound 6 | 11.0 | 1.67 |
| Reference Compound A | 54.7 | 0.78 |

Reference Compound A is disclosed in Burce et al., *Journal of Chromatography,* 137 (1977), 323-332 as NTX-3-terephthaloyl-NTX.

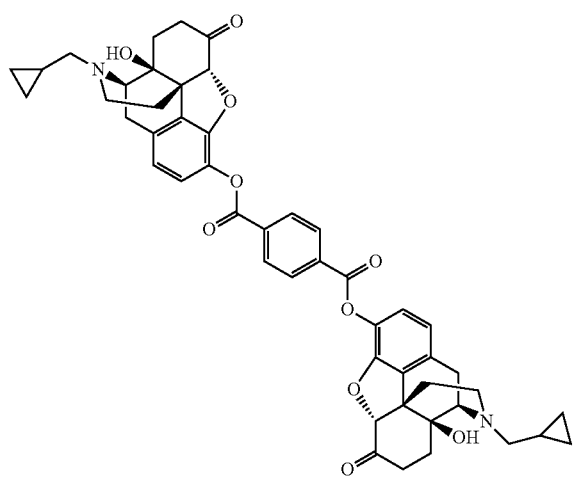

(Reference Compound A)

Example 3: Pharmacokinetic Evaluation of the Release of Naltrexone from Compound 3 in Rats Following a Single Intramuscular Injection Six male Sprague-Dawley rats were allowed to acclimate to the test facility for at least 3 days prior to study start. For dose administration of Compound 3, the rats were lightly anesthetized with isofluorane, the hind leg shaved and dosed intramuscularly with the formulation using a 20 G needle. All animals were observed at dosing and each scheduled collection. Serial whole blood samples were collected via sublingual route (~150 μL) at 1, 8, and 24 hours post dose, and at 2, 4, 7, 10, 15, 22, 24, 28, 35, 42, 49, 56 and 63 days post dose.

Blood samples were placed into K$_2$EDTA blood collection tubes. After collection, blood samples were maintained chilled (on wet ice) and centrifuged (11,500 rpm for 2 minutes at 5 degrees C.) within 30 minutes to obtain plasma. Plasma was transferred into a single vial, 1.5 mL screw cap micro-centrifuge tube with inserts and stored at −80 degrees C. until analysis.

The formulation dosed was a crystalline suspension of Compound 3 (44.4 milligrams of Compound 3 dosed per animal), wherein the crystalline test article was characterized with a particle size distribution of D$_{v10}$=1.6 μm, D$_{v50}$=4.1 μm, and D$_{v90}$=7.7 μm (as measured via laser diffraction). The formulation was prepared the day before dosing. Details of the formulation dosed are described in Table D below.

TABLE D

| Test Article | Naltrexone Dose Level (mg/kg) | Prodrug Conc. (mg/mL) | Dose Volume (mL) | Vehicle | Test Article Storage |
|---|---|---|---|---|---|
| Compound 3 (free base) | 148.07 | 250.0 | 0.25 | 0.1% polysorbate 20, pH 7, 10 mM sodium phosphate buffer | ambient |

Results of the above intramuscular rat study of Compound 3 are shown in Tables E and F. In particular, Table E reports the average blood plasma levels of naltrexone in rat (n=6) over 63 days following intramuscular administration. As shown in Table E, the average blood plasma levels of naltrexone were near or above 1 ng/mL over the 63 day duration. Further, Table F shows the concentrations measured for parent Compound 3, and the resultant intermediate Compound 3i for each animal. As shown in Table F, the concentrations of parent Compound 3 and the resultant intermediate were generally low to not measurable (below the limit of quantitation reported below). These data show efficient conversion of Compound 3 in rats to naltrexone over 63 days with minimal observed plasma concentrations of the intact prodrug (i.e., Compound 3) or its resultant intermediate (i.e., Compound 3i).

TABLE E

| Days | NTX conc. (ng/mL) | Standard Deviation |
|---|---|---|
| 0.042 (1 hour) | 7.43 | 0.87 |
| 0.33 (8 hour) | 6.41 | 0.74 |
| 1 | 6.41 | 1.13 |
| 2 | 6.40 | 1.24 |
| 4 | 13.0 | 4.99 |
| 7 | 19.9 | 10.9 |
| 10 | 15.2 | 8.42 |
| 15 | 7.52 | 4.51 |
| 22 | 4.01 | 1.85 |
| 24 | 4.15 | 2.20 |
| 28 | 3.51 | 2.28 |
| 35 | 3.03 | 2.19 |
| 42 | 2.44 | 1.61 |
| 49 | 1.98 | 1.89 |
| 56 | 0.67 | 0.69 |
| 63 | 1.67 | 0.80 |

TABLE F

| | Compound 3 conc. (ng/mL)* | | | | | | Compound 3i conc. (ng/mL)* | | | | | |
|---|---|---|---|---|---|---|---|---|---|---|---|---|
| Days | Rat 1 | Rat 2 | Rat 3 | Rat 4 | Rat 5 | Rat 6 | Rat 1 | Rat 2 | Rat 3 | Rat 4 | Rat 5 | Rat 6 |
| 0.042 (1 hr) | <0.1 | <0.1 | <0.1 | <0.1 | <0.1 | <0.1 | <0.2 | <0.2 | <0.2 | <0.2 | <0.2 | <0.2 |
| 0.33 (8 hr) | <0.1 | <0.1 | <0.1 | <0.1 | <0.1 | <0.1 | <0.2 | <0.2 | <0.2 | <0.2 | <0.2 | <0.2 |
| 1 | <0.1 | <0.1 | <0.1 | <0.1 | <0.1 | <0.1 | <0.2 | <0.2 | <0.2 | <0.2 | <0.2 | <0.2 |
| 2 | <0.1 | <0.1 | <0.1 | <0.1 | <0.1 | <0.1 | <0.2 | <0.2 | <0.2 | <0.2 | <0.2 | <0.2 |
| 4 | <0.1 | <0.1 | <0.1 | <0.1 | <0.1 | <0.1 | <0.2 | <0.2 | <0.2 | <0.2 | <0.2 | <0.2 |
| 7 | <0.1 | <0.1 | <0.1 | <0.1 | <0.1 | 0.161 | <0.2 | <0.2 | <0.2 | <0.2 | <0.2 | <0.2 |
| 10 | <0.1 | <0.1 | <0.1 | <0.1 | <0.1 | <0.1 | <0.2 | <0.2 | <0.2 | <0.2 | <0.2 | <0.2 |
| 15 | <0.1 | <0.1 | <0.1 | <0.1 | <0.1 | <0.1 | <0.2 | <0.2 | <0.2 | <0.2 | <0.2 | <0.2 |
| 22 | <0.1 | <0.1 | <0.1 | <0.1 | <0.1 | <0.1 | <0.2 | <0.2 | <0.2 | <0.2 | <0.2 | <0.2 |
| 24 | <0.1 | <0.1 | <0.1 | <0.1 | <0.1 | <0.1 | <0.2 | <0.2 | <0.2 | <0.2 | <0.2 | <0.2 |
| 28 | <0.1 | <0.1 | <0.1 | <0.1 | <0.1 | <0.1 | <0.2 | <0.2 | <0.2 | <0.2 | <0.2 | <0.2 |
| 35 | <0.1 | <0.1 | <0.1 | <0.1 | <0.1 | <0.1 | <0.2 | <0.2 | <0.2 | <0.2 | <0.2 | <0.2 |
| 42 | <0.1 | <0.1 | <0.1 | 0.128 | <0.1 | <0.1 | 0.805 | 0.149 | <0.2 | <0.2 | <0.2 | <0.2 |
| 49 | 0.134 | 0.131 | 0.138 | <0.1 | 0.143 | <0.1 | 0.423 | <0.2 | <0.2 | <0.2 | <0.2 | <0.2 |
| 56 | 2.02 | 0.753 | 0.501 | 0.281 | 0.245 | 0.237 | <0.2 | <0.2 | <0.2 | <0.2 | <0.2 | <0.2 |
| 63 | 0.184 | 0.229 | 0.223 | 0.234 | 0.255 | 0.207 | <0.2 | <0.2 | <0.2 | <0.2 | <0.2 | <0.2 |

*Values with a "<" sign indicate concentrations below the limit of quantitation

Example 4: Characterization and Crystallization Method for Compound 3

Compound 3 was crystallized according to the following procedure. 86.1 mL of dimethylacetamide was added to 11.229 grams of Compound 3. The mixture was stirred, sonicated, and mixed with a homogenizer to form a milky suspension at room temperature. The mixture was stirred on a hot plate set to 50 degrees C. until a hazy brown solution was achieved. The hazy solution was polish filtered (glass fiber 1 micron pore size, 25 mm syringe filter (2 filters used)) while still warm into a 500 mL flask. A clear brown solution resulted. An equal volume of isopropanol (86 mL) was added at room temperature as a single aliquot with stirring. A cloudy precipitate was observed at the interface of the solvent and antisolvent that immediately cleared. Solution was still clear after antisolvent addition. Solution began to become cloudy within 5 minutes of antisolvent addition and slowly became more cloudy over time. After 1.3 hours, a second volume of isopropanol (86 mL) was added at room temperature as a single aliquot with stirring. After 1 hour, a third volume of isopropanol (86 mL) was added at room temperature as a single aliquot with stirring. A temperature probe was added to the slurry and the temperature on the stir plate was set to 40 degrees C. After 20 minutes, the heat was turned off. After cooling to room temperature, the sample was vacuum filtered using a polypropylene filter funnel with 10 micron polyethylene fritted disk. The resultant filter cake was washed with room temperature isopropanol (approximately 300 mL) resulting in a mother liquor that was slightly hazy. The filter cake was broken up with a spatula and the entire filter was placed in a vacuum oven to dry overnight at 40 degrees C. with a nitrogen bleed. The material was dried overnight.

FIG. 1 shows a powder x-ray diffraction (PXRD) pattern of the crystalline form. The PXRD pattern was collected using a Rigaku Miniflex II Desktop X-ray diffractometer, with CuKα radiation at 15 mA and 30 kV. Each sample was mounted on a zero background sample holder. A scan speed of 7.5°/min 2-theta was chosen, coupled with a sampling width of 0.2° 2-theta and a start and stop angle of 2 degrees and 40 degrees 2-theta. The crystalline form of Compound 3 can also be characterized by any one, any two, any three, any four, any five, or any six or more of the peaks in the PXRD diffractogram in FIG. 1 including, but not limited to, 7.45 11.24, 12.05, 12.98, 14.98, 16.06, 17.18, 18.41, 18.93, 20.31, 20.49, 21.96 and 22.70 degrees 2-theta (±0.2 degrees).

For example, in one embodiment, the crystalline form of Compound 3 can be characterized by the PXRD peaks at 7.45, 11.24, 12.98, and 16.06 degrees 2-theta (±0.2 degrees). In another embodiment, the crystalline form of Compound 3 can be characterized by the PXRD peaks at 12.05, 14.98, 17.18 and 18.93 degrees 2-theta (±0.2 degrees). In another embodiment, the crystalline form of Compound 3 can be characterized by the PXRD peaks at 7.45, 12.05, 14.98 and 16.06 degrees 2-theta (±0.2 degrees).

Differential scanning calorimetry (DSC) was also performed on the crystalline form of Compound 3. An endotherm was measured with an onset temperature at 194.5 degrees C. and a melt temperature at 196.9 degrees C. The DSC thermogram was measured with a TA Instruments Q2000 DSC. An approximately 3-6 mg sample was accurately weighed into a hermetic pan. Dry nitrogen was used as a purge gas (50 mL/min nitrogen) and a heating rate of 1 or 5 degrees C. min$^{-1}$ up to 300 degrees C. was applied.

While this invention has been particularly shown and described with references to preferred embodiments thereof, it will be understood by those skilled in the art that various changes in form and details may be made therein without departing from the scope of the invention encompassed by the appended claims.

What is claimed:

1. A compound of Formula Ic:

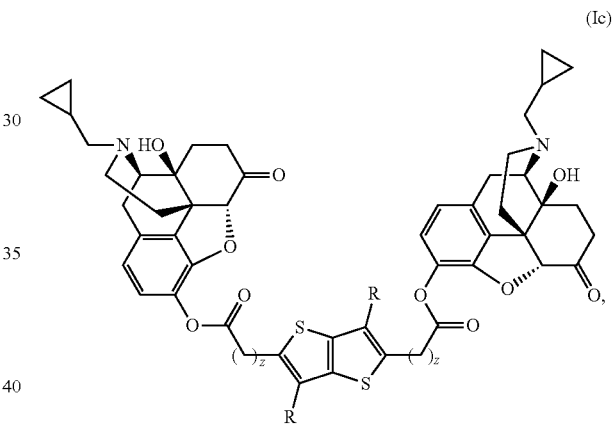

(Ic)

or a pharmaceutically acceptable salt thereof;
  wherein:
    both R groups, always being the same, are selected from hydrogen, halogen, or unsubstituted $C_1$-$C_4$ alkyl; and
    both values of z, always being the same, are 1, 2, 3, or 4.

2. The compound of claim 1, wherein both R groups are hydrogen.

3. The compound of claim 1, wherein both R groups are halogen.

4. The compound of claim 1, wherein both R groups are unsubstituted $C_1$-$C_4$ alkyl.

5. The compound of claim 1, wherein both R groups are methyl.

6. The compound of claim 1, wherein both values of z are 1.

7. The compound of claim 1, wherein both values of z are 2.

8. A compound of claim 1 selected from the group consisting of:

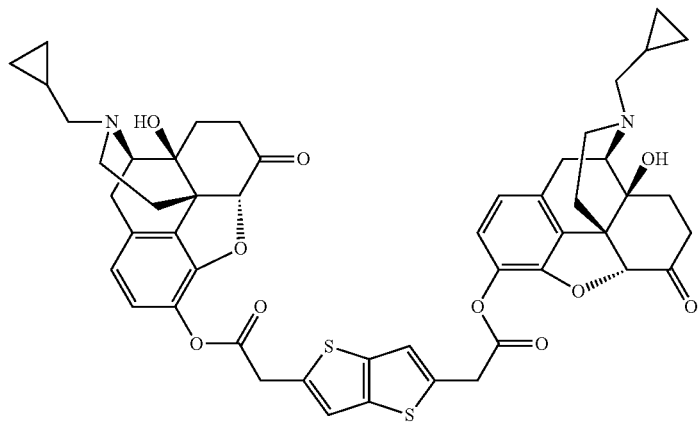
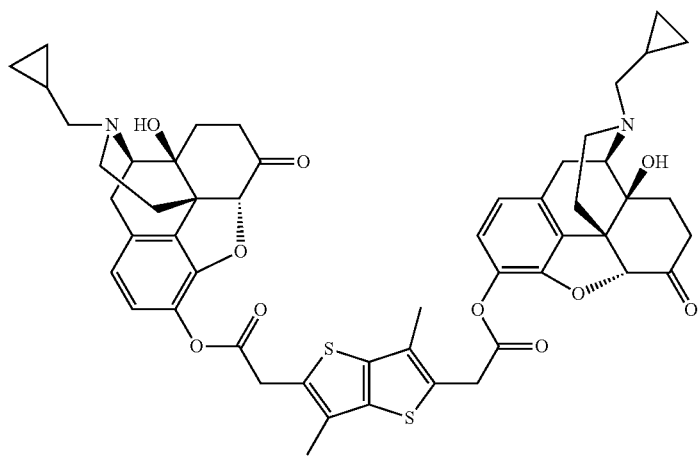
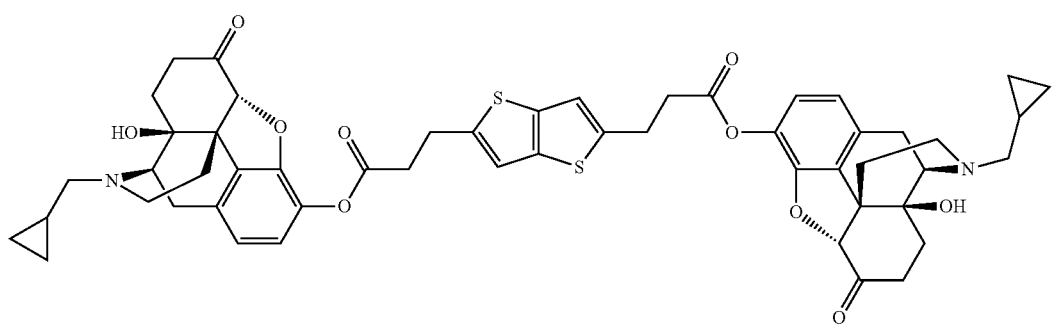 [SMILES: O=C(CCc1sc2c(Cl)c(CCC(=O)Oc3ccc4c5c3O[C@H]3C(=O)CC[C@@]6(O)[C@@H](C4)N(CC4CC4)CC[C@]536)sc2c1Cl)Oc1ccc2c3c1O[C@H]1C(=O)CC[C@@]4(O)[C@@H](C2)N(CC2CC2)CC[C@]314]
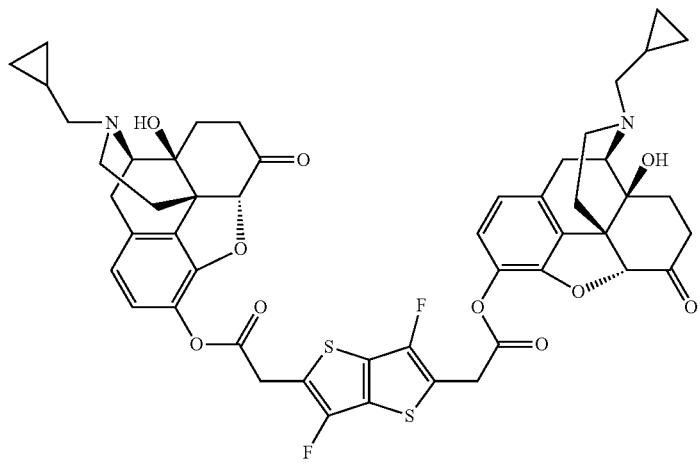

-continued

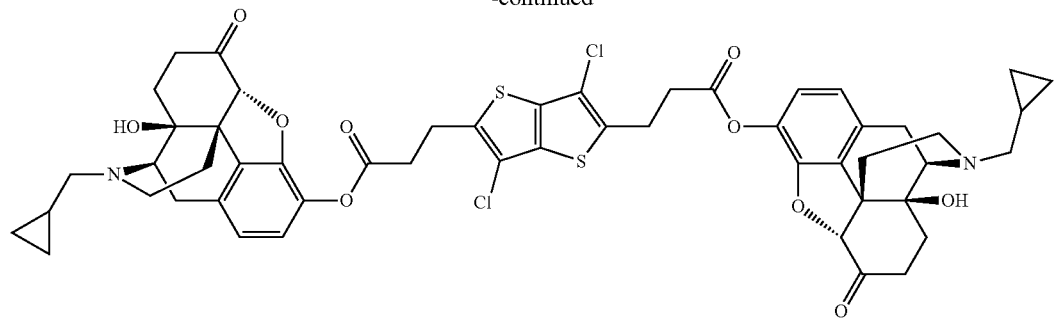

and a pharmaceutically acceptable salt thereof.

9. A pharmaceutical composition comprising a compound of claim 1 and a pharmaceutically acceptable carrier.

10. The pharmaceutical composition of claim 9, wherein the composition is adapted for parenteral administration.

11. The pharmaceutical composition of claim 10, wherein the composition provides a duration of release of naltrexone of about 9 weeks following parenteral administration.

12. The pharmaceutical composition of claim 10, wherein the composition provides a duration of release of naltrexone of about 13 weeks following parenteral administration.

13. The pharmaceutical composition of claim 10, wherein the parenteral administration is an intramuscular injection.

* * * * *